United States Patent
Jung et al.

(10) Patent No.: US 11,479,562 B2
(45) Date of Patent: Oct. 25, 2022

(54) HETEROCYCLIC COMPOUND AND ORGANIC LIGHT-EMITTING DEVICE COMPRISING SAME

(71) Applicant: LG CHEM, LTD., Seoul (KR)

(72) Inventors: Min Woo Jung, Daejeon (KR); Wanpyo Hong, Daejeon (KR); Dong Hoon Lee, Daejeon (KR); Boonjae Jang, Daejeon (KR); Jungha Lee, Daejeon (KR); Su Jin Han, Daejeon (KR); Seulchan Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 323 days.

(21) Appl. No.: 16/763,303

(22) PCT Filed: Mar. 28, 2019

(86) PCT No.: PCT/KR2019/003667
§ 371 (c)(1),
(2) Date: May 12, 2020

(87) PCT Pub. No.: WO2019/190241
PCT Pub. Date: Oct. 3, 2019

(65) Prior Publication Data
US 2021/0070768 A1    Mar. 11, 2021

(30) Foreign Application Priority Data
Mar. 28, 2018 (KR) .................. 10-2018-0035680

(51) Int. Cl.
*C07D 495/04* (2006.01)
*H01L 51/00* (2006.01)
(52) U.S. Cl.
CPC ........ *C07D 495/04* (2013.01); *H01L 51/0067* (2013.01); *H01L 51/0072* (2013.01); *H01L 51/0073* (2013.01); *H01L 51/0074* (2013.01)

(58) Field of Classification Search
CPC .............. C07D 495/04; H01L 51/0067; H01L 51/0072–0074
(Continued)

(56) References Cited

U.S. PATENT DOCUMENTS

| 9,755,159 B2 | 9/2017 | Dyatkin et al. |
| 10,177,316 B2 | 1/2019 | Zeng et al. |

(Continued)

FOREIGN PATENT DOCUMENTS

| JP | 2015134745 | 7/2015 |
| KR | 10-20150136942 | 12/2015 |

(Continued)

OTHER PUBLICATIONS

Office Action of Chinese Patent Office in Appl'n No. 201980005357.X, dated Dec. 22, 2021.

*Primary Examiner* — Sheng-Bai Zhu
(74) *Attorney, Agent, or Firm* — Dentons US LLP

(57) ABSTRACT

Provided is a compound of

Chemical Formula 1

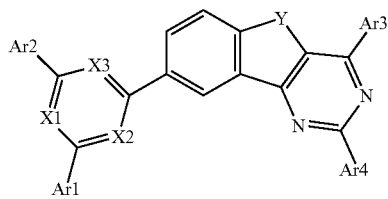

wherein:
Y is O or S;
X1 to X3 are each N or CH, and one or more of X1 to X3 is N; and (Continued)

Ar1 to Ar4 are the same as or different from each other, and each independently is an aryl group having 6 to 20 carbon atoms that is unsubstituted or substituted with nitrile or a heteroaryl group having 2 to 20 carbon atoms; or a tricyclic heteroaryl group having 2 to 20 carbon atoms that is unsubstituted or substituted with an aryl group having 6 to 20 carbon atoms, and an organic light emitting device including the same.

7 Claims, 1 Drawing Sheet

(58) Field of Classification Search
USPC .......................................... 257/40
See application file for complete search history.

(56) References Cited

U.S. PATENT DOCUMENTS 10,319,921 B2  6/2019  Kang et al.
2010/0219404 A1* 9/2010 Endo .................. H01L 51/0072
                                                       257/E51.027
2015/0243893 A1  8/2015  Joseph et al.
2016/0111661 A1* 4/2016 Boudreault ......... C07F 15/0033
                                                       546/4
2016/0329502 A1* 11/2016 Dyatkin ............... C09K 11/025
2017/0186971 A1  6/2017  Kanamoto et al.
2017/0200903 A1  7/2017  Park et al.

FOREIGN PATENT DOCUMENTS

| KR | 10-2016-0026661 | 3/2016 |
| KR | 10-20160098064 | 8/2016 |
| KR | 10-20170005637 | 1/2017 |
| KR | 10-20170068927 | 6/2017 |
| KR | 10-20150088176 | 7/2017 |
| KR | 10-20180009596 | 1/2018 |
| WO | 2015-037675 | 3/2015 |
| WO | 2015-182872 | 12/2015 |
| WO | 2017-109637 | 6/2017 |

* cited by examiner

【FIG. 1】
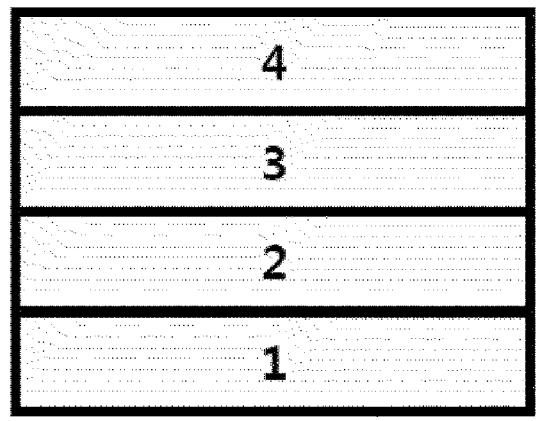
【FIG. 2】
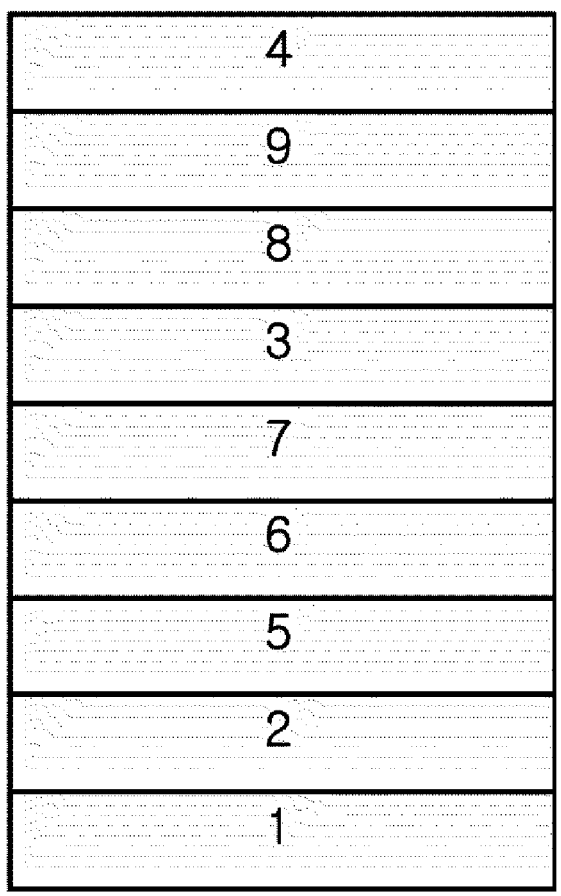

HETEROCYCLIC COMPOUND AND ORGANIC LIGHT-EMITTING DEVICE COMPRISING SAME

CROSS-REFERENCE TO RELATED APPLICATIONS

This application is a National Stage Application of International Application No. PCT/KR2019/003667 filed on Mar. 28, 2019, which claims priority to and the benefits of Korean Patent Application No. 10-2018-0035680, filed with the Korean Intellectual Property Office on Mar. 28, 2018, the entire contents of which are incorporated herein by reference.

TECHNICAL FIELD

The present specification relates to a heterocyclic compound, and an organic light emitting device including the same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

BRIEF SUMMARY

Technical Problem

The present specification is directed to providing a compound, and an organic light emitting device including the same.

Technical Solution

One embodiment of the present specification provides a compound of Chemical Formula 1:

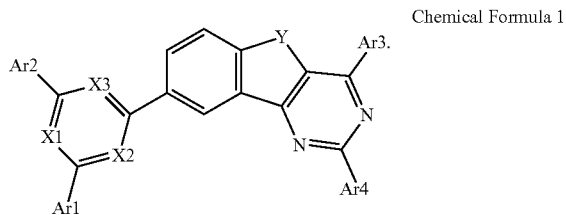

Chemical Formula 1

In Chemical Formula 1:

Y is O or S;

X1 to X3 are each N or CH, and one or more of X1 to X3 are N;

Ar1 to Ar4 are the same as or different from each other, and each independently is an aryl group having 6 to 20 carbon atoms that is unsubstituted or substituted with nitrile or a heteroaryl group having 2 to 20 carbon atoms; or a tricyclic heteroaryl group having 2 to 20 carbon atoms that is unsubstituted or substituted with an aryl group having 6 to 20 carbon atoms.

Another embodiment of the present specification provides an organic light emitting device including a first electrode; a second electrode provided opposite to the first electrode; and one or more organic material layers provided between the first electrode and the second electrode, wherein one or more layers of the organic material layers include the compound of Chemical Formula 1.

Advantageous Effects

A compound according to one embodiment of the present specification can be used as a material of an organic material layer of an organic light emitting device, and by using the same, efficiency can be enhanced, a low driving voltage can be obtained, and/or lifetime properties can be enhanced in the organic light emitting device.

DESCRIPTION OF DRAWINGS

FIGS. 1 and 2 illustrate organic light emitting devices according to embodiments of the present specification.

REFERENCE NUMBERS

1: Substrate
2: The First Electrode
3: Light Emitting Layer
4: The Second Electrode
5: Hole Injection Layer
6: Hole Transfer Layer
7: Electron Blocking Layer
8: Electron Transfer Layer
9: Electron Injection Layer

DETAILED DESCRIPTION

Hereinafter, the present specification will be described in more detail.

One embodiment of the present specification provides a compound of Chemical Formula 1.

By having an electron deficient group-electron deficient group-electron donating group structure, the compound of Chemical Formula 1 of the present specification is capable of controlling a total electron quantity in a device and thereby maximizing efficiency and lifetime.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which a hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of hydrogen, deuterium, a nitrile group, a substituted or unsubstituted alkyl group, a substituted or unsubstituted cycloalkyl group, a substituted or unsubstituted alkoxy group, a substituted or unsubstituted aryloxy group, a substituted or unsubstituted aryl group, and a substituted or unsubstituted heterocyclic group, or being substituted with a substituent linking two or more substituents among the substituents described above, or having no substituents. For example, "a substituent linking two or more substituents" can include an aryl group substituted with an aryl group, an aryl group substituted with a heteroaryl group, a heterocyclic group substituted with an aryl group, an aryl group substituted with an alkyl group, and the like.

In the present specification, the alkyl group can be linear or branched, and although not particularly limited thereto, the number of carbon atoms is preferably from 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butyl-cyclohexyl, cycloheptyl, cyclooctyl and the like, but are not limited thereto.

In the present specification, the alkoxy group can be linear, branched or cyclic. The number of carbon atoms of the alkoxy group is not particularly limited, but is preferably from 1 to 30. Specific examples thereof can include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethyl-butyloxy, n-octyloxy, n-nonyloxy, n-decyloxy, benzyloxy, p-methylbenzyloxy and the like, but are not limited thereto.

In the present specification, the aryl group is not particularly limited, but preferably has 6 to 30 carbon atoms, and the aryl group can be monocyclic or polycyclic.

When the aryl group is a monocyclic aryl group, the number of carbon atoms is not particularly limited, but is preferably from 6 to 30. Specific examples of the monocyclic aryl group can include a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group can include a naphthyl group, an anthracenyl group, a phenanthryl group, a triphenyl group, a pyrenyl group, a phenalenyl group, a perylenyl group, a chrysenyl group, a fluorenyl group and the like, but are not limited thereto.

In the present specification, the fluorenyl group can be substituted, and adjacent groups can bond to each other to form a ring.

When the fluorenyl group is substituted,

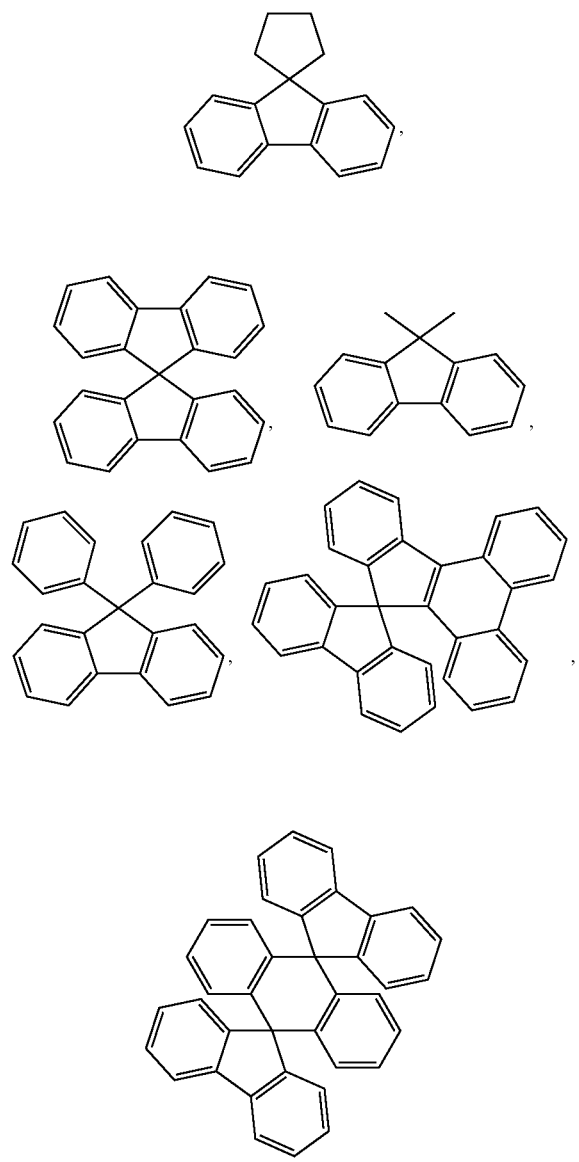

and the like can be included. However, the structure is not limited thereto.

In the present specification, the aryl group in the aryloxy group, the N-arylalkylamine group and the N-arylheteroarylamine group is the same as the examples of the aryl group described above. Specific examples of the aryloxy group can include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like.

In the present specification, the heteroaryl group includes one or more atoms that are not carbon, that is, heteroatoms, and specifically, the heteroatom can include one or more heteroatoms selected from the group consisting of O, N, Se, S and the like. The number of carbon atoms is not particularly limited, but is preferably from 2 to 30, and the heteroaryl group can be monocyclic or polycyclic. Examples of the heterocyclic group can include a thiophene group, a furan group, a pyrrole group, an imidazole group, a triazole group, an oxazole group, an oxadiazole group, a pyridyl group, a bipyridyl group, a pyrimidyl group, a triazinyl group, a triazole group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazole group, a benzoxazole group, a benzimidazole group, a benzothiazole group, a benzocarbazole group, a dibenzopyrrole group, an indole group, a benzothiophene group, a dibenzothiophene group, a benzofuran group, a benzoquinolyl group, a benzonaphthothiophene group, a benzonaphthofuran group, a phenanthrolinyl group, an isoxazole group, a thiadiazole group, a phenoxazine group, a phenothiazine group, a dibenzofuran group and the like, but are not limited thereto.

According to one embodiment of the present specification, the compound of Chemical Formula 1 is a compound of the following Chemical Formula 2 or 3:

Chemical Formula 2

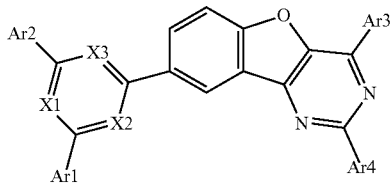

Chemical Formula 3

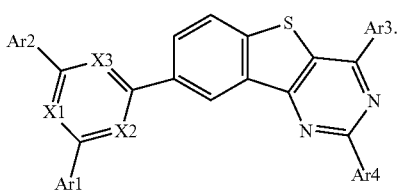

In Chemical Formulae 2 and 3, the substituents have the same definitions as in Chemical Formula 1.

According to one embodiment of the present specification, X1, X2 and X3 are N.

According to one embodiment of the present specification, two of X1 to X3 are N, and the remaining one is CH. For example, X1 is CH, and X2 and X3 are N, or X2 is CH, and X1 and X3 are N.

According to one embodiment of the present specification, Ar1 to Ar4 are the same as or different from each other, and each independently is an aryl group having 6 to 20 carbon atoms that is unsubstituted or substituted with nitrile or a heteroaryl group having 2 to 20 carbon atoms; or a tricyclic heteroaryl group having 2 to 20 carbon atoms that is unsubstituted or substituted with an aryl group having 6 to 20 carbon atoms.

According to one embodiment of the present specification, Ar1 to Ar4 are the same as or different from each other, and each independently is a phenyl group that is unsubstituted or substituted with a nitrile group or a carbazole group, a biphenyl group, a carbazole group, a dibenzofuran group or a dibenzothiophene group.

According to one embodiment of the present specification, Ar1 to Ar4 are the same as or different from each other, and each independently a phenyl group that is unsubstituted or substituted with a nitrile group or a 9-carbazole group; a biphenyl group; a 9-carbazole group; a 1-carbazole group; a 2-carbazole group; a 3-carbazole group; a 4-carbazole group; a 4-dibenzofuran group; or a 4-dibenzothiophene group.

According to one embodiment of the present specification, at least one of Ar1 to Ar4 is a heteroaryl group, or an aryl group substituted with a nitrile group or a heteroaryl group, and the rest are an aryl group.

According to one embodiment of the present specification, one of Ar1 to Ar4 is a heteroaryl group, or an aryl group substituted with a nitrile group or a heteroaryl group, and the rest are an aryl group.

According to one embodiment of the present specification, at least one of Ar1 to Ar4 is a carbazole group, a phenyl group substituted with a carbazole group or a nitrile group, a dibenzofuran group, or a dibenzothiophene group, and the rest are an aryl group.

According to one embodiment of the present specification, one of Ar1 to Ar4 is a carbazole group, a phenyl group substituted with a carbazole group or a nitrile group, a dibenzofuran group, or a dibenzothiophene group, and the rest are an aryl group.

According to one embodiment of the present specification, at least one of Ar1 to Ar4 is a carbazole group, a phenyl group substituted with a carbazole group or a nitrile group, a dibenzofuran group, or a dibenzothiophene group, and the rest are a phenyl group or a biphenyl group.

According to one embodiment of the present specification, one of Ar1 to Ar4 is a carbazole group, a phenyl group substituted with a carbazole group or a nitrile group, a dibenzofuran group, or a dibenzothiophene group, and the rest are a phenyl group or a biphenyl group.

According to one embodiment of the present specification, Ar1 to Ar4 are an aryl group.

According to one embodiment of the present specification, Ar1 to Ar4 are a phenyl group or a biphenyl group.

According to one embodiment of the present specification, Ar1 to Ar4 are a phenyl group.

According to one embodiment of the present specification, at least one of Ar1 to Ar4 is a biphenyl group, and the rest are a phenyl group.

According to one embodiment of the present specification, one of Ar1 to Ar4 is a biphenyl group, and the rest are a phenyl group.

According to one embodiment of the present specification, a compound of Chemical Formula 1 is selected from among the following compounds:

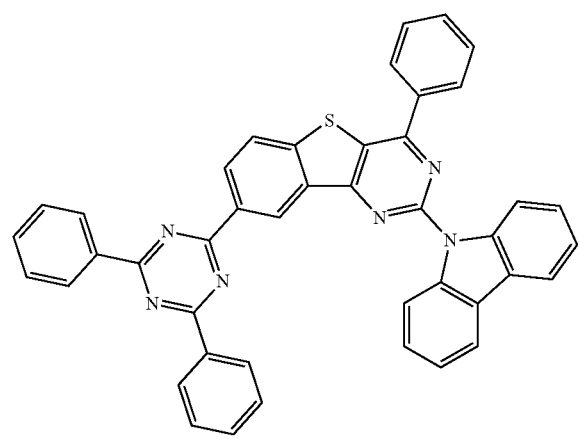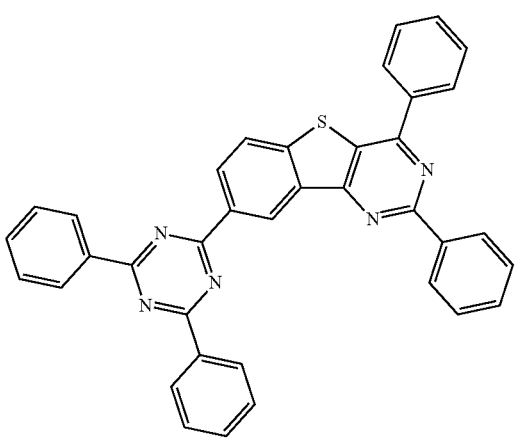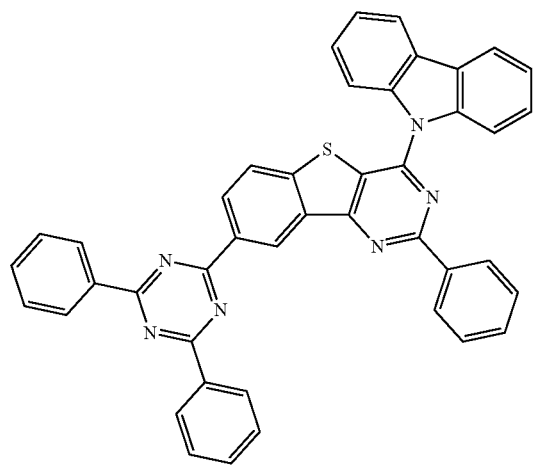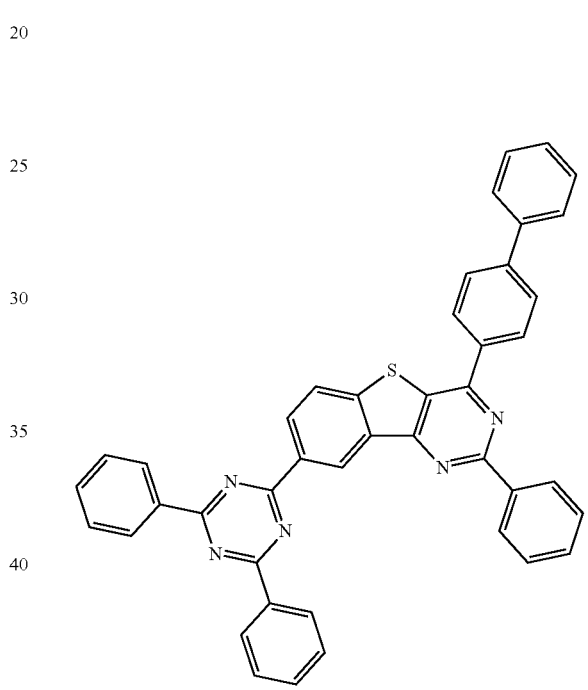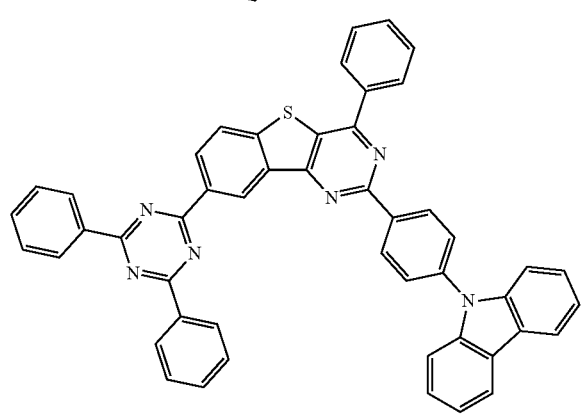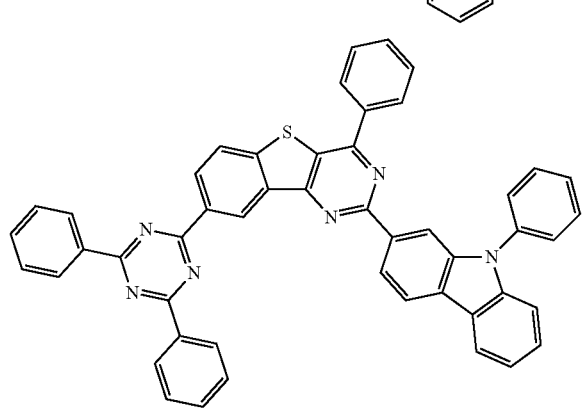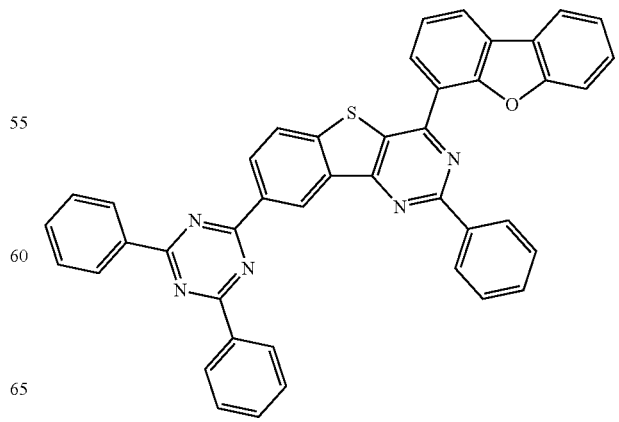

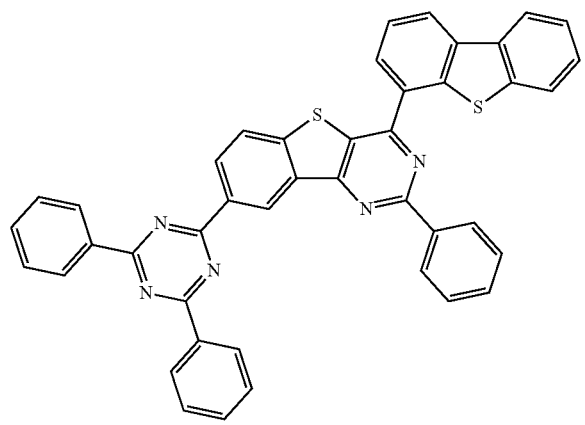
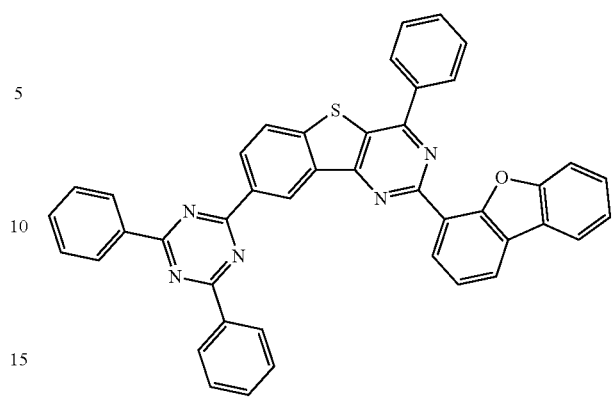
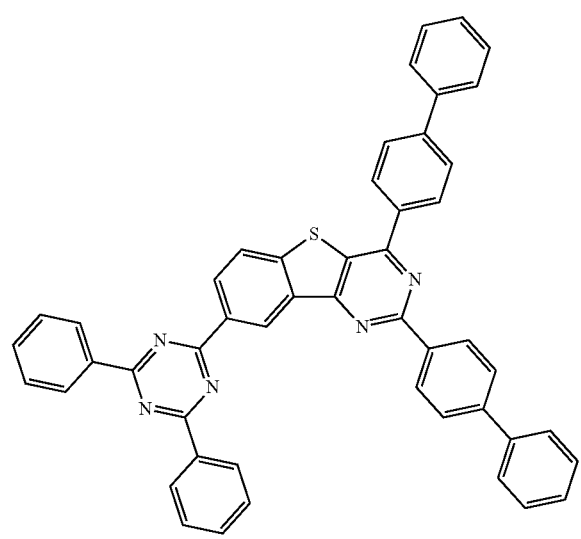
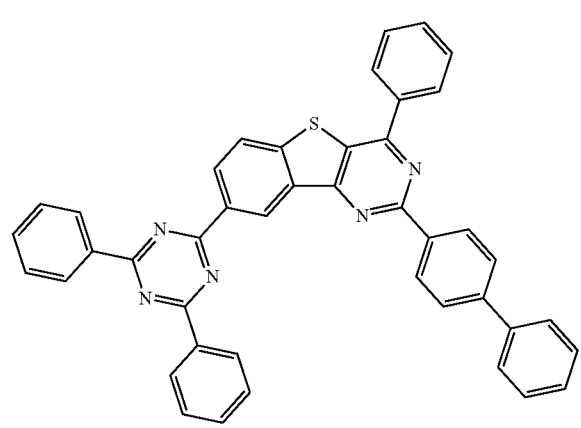
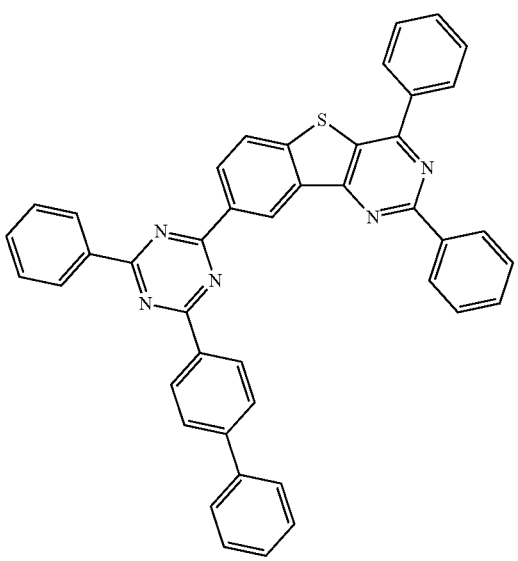

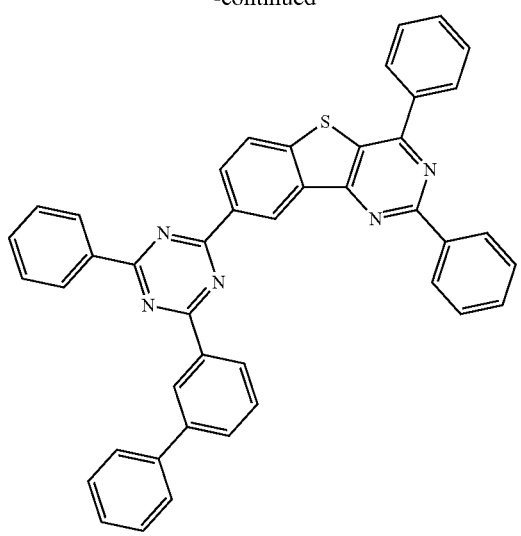
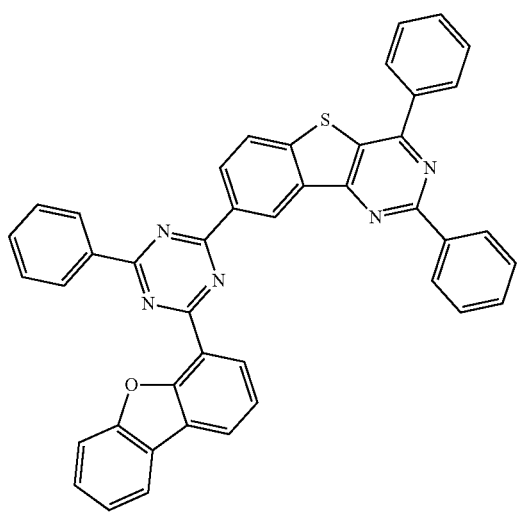
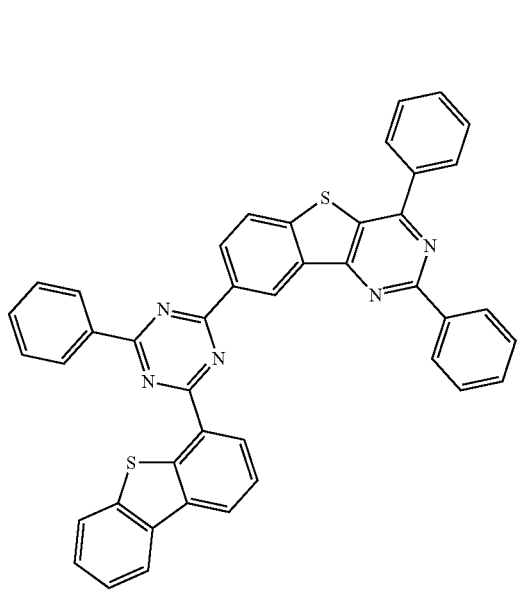
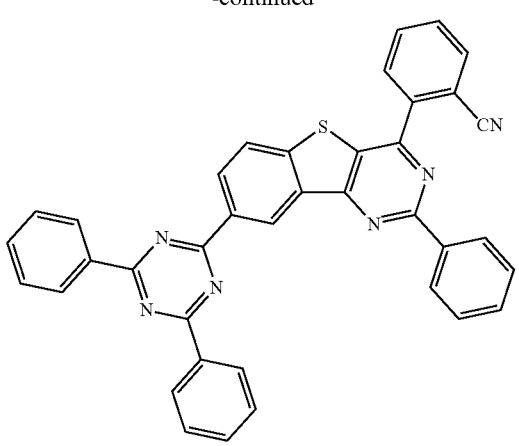
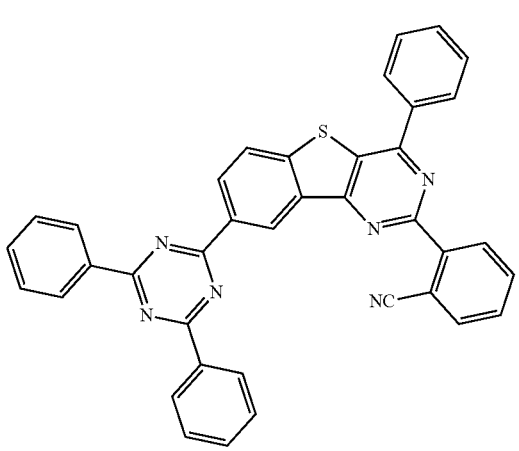
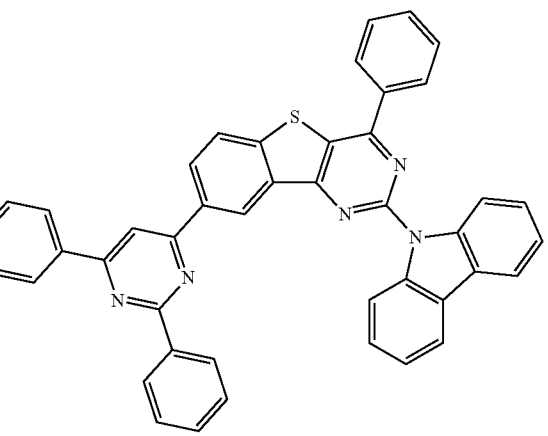

-continued

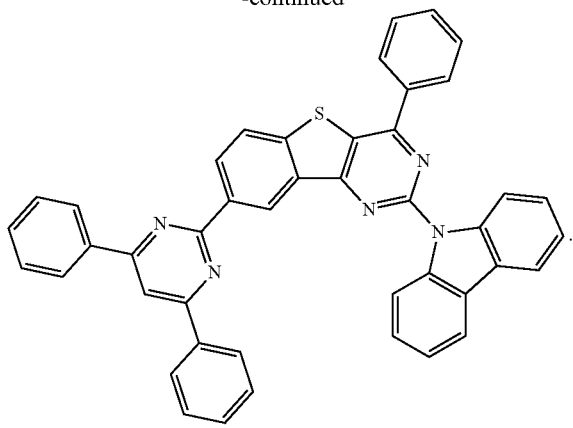

One embodiment of the present specification provides an organic light emitting device including a first electrode; a second electrode provided opposite to the first electrode; and one or more organic material layers provided between the first electrode and the second electrode, wherein one or more layers of the organic material layers include the compound described above.

According to one embodiment of the present specification, the organic material layer of the organic light emitting device of the present specification can be famed in a single layer structure, but can also be formed in a multilayer structure in which two or more organic material layers are laminated. For example, the organic light emitting device of the present disclosure can have a structure including a hole injection layer, a hole transfer layer, an electron blocking layer, a light emitting layer, a hole blocking layer, an electron transfer layer, an electron injection layer and the like as the organic material layer. However, the structure of the organic light emitting device is not limited thereto, and can include a smaller or a larger number of organic material layers.

For example, the organic light emitting device of the present specification can have structures as illustrated in FIG. 1 and FIG. 2, however, the structure is not limited thereto.

FIG. 1 illustrates a structure of the organic light emitting device in which a first electrode (2), a light emitting layer (3) and a second electrode (4) are consecutively laminated on a substrate (1). FIG. 1 is an exemplary structure of the organic light emitting device according to one embodiment of the present specification, and other organic material layers can be further included. In such a structure, the compound of Chemical Formula 1 can be included in the light emitting layer.

FIG. 2 illustrates a structure of the organic light emitting device in which a first electrode (2), a hole injection layer (5), a hole transfer layer (6), an electron blocking layer (7), a light emitting layer (3), an electron transfer layer (8), an electron injection layer (9) and a second electrode (4) are consecutively laminated on a substrate (1). FIG. 2 is an exemplary structure of the organic light emitting device according to an embodiment of the present specification, and other organic material layers can be further included. Herein, the compound of Chemical Formula 1 can be included in the hole injection layer, the hole transfer layer, the light emitting layer, or the electron injection and transfer layer. The compound of Chemical Formula 1 can be preferably included in the light emitting layer.

According to one embodiment of the present specification, the organic material layer includes a hole injection layer, a hole transfer layer or an electron blocking layer, and the hole injection layer, the hole transfer layer or the electron blocking layer includes the compound of Chemical Formula 1.

According to one embodiment of the present specification, the organic material layer includes a light emitting layer, and the light emitting layer includes the compound of Chemical Formula 1.

According to one embodiment of the present specification, the organic material layer includes a light emitting layer, and the light emitting layer includes the compound of Chemical Formula 1 as a host of the light emitting layer.

According to one embodiment of the present specification, the organic material layer includes a light emitting layer, and the light emitting layer can include the compound of Chemical Formula 1, an additional host material and an additional dopant material.

According to one embodiment of the present specification, the host material added to the light emitting layer includes a carbazole-based compound and the like.

According to one embodiment of the present specification, the dopant material added to the light emitting layer includes a metal complex compound such as an iridium-based complex compound.

According to one embodiment of the present specification, when the light emitting layer include a plurality of hosts, the first host and the second host have a mass ratio of 50:50.

According to one embodiment of the present specification, the light emitting layer includes the dopant in a ratio of 1% to 20% with respect to a total mass of the host and the dopant.

According to one embodiment of the present specification, the organic material layer includes a hole blocking layer, an electron transfer layer, an electron injection layer, or an electron injection and transfer layer, and the hole blocking layer, the electron transfer layer, the electron injection layer, or the electron injection and transfer layer includes the compound of Chemical Formula 1.

According to one embodiment of the present specification, the electron transfer layer, the electron injection layer, or the electron injection and transfer layer including the compound of Chemical Formula 1 can further include an n-type dopant. As the n-type dopant, those known in the art can be used, and for example, alkali metals, alkaline earth metals, alkali metal compounds, alkaline earth metal compounds, alkali metal complexes, alkaline earth metal complexes or the like can be used. As the metal compound, oxides, halides and the like can be used, and the complex can further include an organic ligand. For example, LiQ and the like can be used. The n-type dopant can be included in the electron transfer layer, the electron injection layer, or the electron injection and transfer layer in 1% by weight to 75% by weight and preferably in 30% by weight to 55% by weight.

According to one embodiment of the present specification, the organic material layer can further include one or more layers selected from the group consisting of a hole injection layer, a hole transfer layer, an electron blocking layer, a hole blocking layer, an electron transfer layer and an electron injection layer.

The organic light emitting device of the present specification can be manufactured using materials and methods known in the art, except that one of more layers of the organic material layers include the compound of the present specification, that is, the compound of Chemical Formula 1.

When the organic light emitting device includes a plurality of organic material layers, the organic material layers can be formed with the same material or with different materials.

For example, the organic light emitting device of the present specification can be manufactured by consecutively laminating a first electrode, an organic material layer and a second electrode on a substrate. Herein, the organic light emitting device can be manufactured by forming the first electrode on the substrate by depositing a metal, a metal oxide having conductivity, or an alloy thereof using a physical vapor deposition (PVD) method such as a sputtering method or an e-beam evaporation method, forming the organic material layer including a hole injection layer, a hole transfer layer, a light emitting layer and an electron transfer layer thereon, and then depositing a material usable as the second electrode thereon. In addition to this method, the organic light emitting device can be manufactured by consecutively depositing a second electrode material, an organic material layer and a first electrode material on a substrate. In addition, the compound of Chemical Formula 1 can be formed into the organic material layer using a solution coating method as well as a vacuum deposition method when manufacturing the organic light emitting device. Herein, the solution coating method means spin coating, dip coating, doctor blading, ink jet printing, screen printing, a spray method, roll coating and the like, but is not limited thereto.

According to one embodiment of the present specification, the first electrode is an anode, and the second electrode is a cathode.

According to another embodiment of the present specification, the first electrode is a cathode, and the second electrode is an anode.

As the anode material, materials having large work function are normally preferred so that hole injection to an organic material layer is smooth. Specific examples of the anode material usable in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)-thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al, $LiO_2$/Al or Mg/Ag, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

The light emitting material of the light emitting layer is a material capable of emitting light in a visible region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxy-quinoline aluminum complexes ($Alq_3$); carbazole series compounds; dimerized styryl compounds; BAlq; 10-hydroxybenzoquinoline-metal compounds; benzoxazole, benzothiazole and benzimidazole series compounds; poly(p-phenylenevinylene) (PPV) series polymers; spiro compounds; polyfluorene, rubrene, and the like, but are not limited thereto.

The light emitting layer can include a host material and a dopant material. The host material can include fused aromatic ring derivatives, heteroring-containing compounds or the like. Specifically, as the fused aromatic ring derivative, anthracene derivatives, pyrene derivatives, naphthalene derivatives, pentacene derivatives, phenanthrene compounds, fluoranthene compounds and the like can be included, and as the heteroring-containing compound, carbazole derivatives, dibenzofuran derivatives, ladder-type furan compounds, pyrimidine derivatives and the like can be included, however, the host material is not limited thereto.

The dopant material can include aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group, and arylamino group-including pyrene, anthracene, chrysene, peryflanthene and the like can be included. The styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group can be substituted or unsubstituted. Specifically, styrylamine, styryldiamine, styryltriamine, styryltetramine and the like can be included, however, the styrylamine compound is not limited thereto. As the metal complex, iridium complexes, platinum complexes and the like can be included, however, the metal complex is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suited.

Specific examples thereof include Al complexes of 8-hydroxyquinoline; complexes including Alq$_3$; organic radical compounds; hydroxyflavon-metal complexes, and the like, but are not limited thereto. The electron transfer layer can be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and as the electron injection material, compounds having an electron transferring ability, having an electron injection effect from a cathode, having an excellent electron injection effect for a light emitting layer or light emitting material, and preventing excitons generated in the light emitting layer from moving to a hole injection layer, and in addition thereto, having an excellent thin film forming ability are preferred. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxy-quinolinato)copper, bis(8-hydroxyquinolinato)manganese, tris-(8-hydroxyquinolinato)aluminum, tris(2-methyl-8-hydroxy-quinolinato)aluminum, tris(8-hydroxyquinolinato)gallium, bis(10-hydroxybenzo[h]quinolinato)beryllium, bis(10-hydroxy-benzo[h]quinolinato)zinc, bis(2-methyl-8-quinolinato)-chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium and the like, but is not limited thereto.

The organic light emitting device according to the present specification can be a top-emission type, a bottom-emission type or a dual-emission type depending on the materials used.

EXAMPLES

Hereinafter, the present specification will be described in detail with reference to examples. However, the examples according to the present specification can be modified to various other forms, and the scope of the present specification is not to be construed as being limited to the examples described below. Examples of the present specification are provided in order to more fully describe the present specification to those having average knowledge in the art.

Synthesis Example

Preparation Example 1

1) Synthesis of Compound 1-1

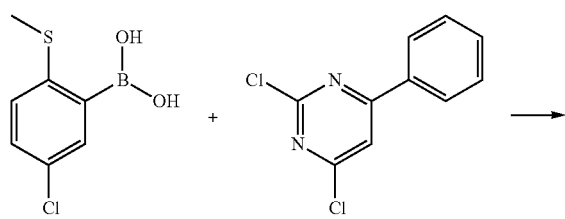

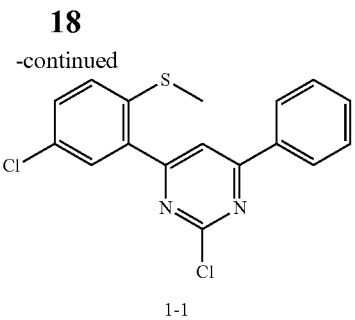

After dispersing 2,4-dichloro-6-phenylpyrimidine (50.0 g, 223.2 mmol) and (5-chloro-2-(methylthio)phenyl)boronic acid (45.1 g, 223.2 mmol) into tetrahydrofuran (500 ml), a 2 M aqueous potassium carbonate solution (aq. K$_2$CO$_3$) (335 ml) and then tetrakis(triphenylphosphine)palladium(0) [Pd(PPh$_3$)$_4$] (7.7 g, 3 mol %) were added thereto, and the result was stirred under reflux for 5 hours. After lowering the temperature to room temperature, the result was separated into an organic layer and a water layer, and the organic layer was distilled. The distilled organic material was extracted with chloroform and water, and after distilling the chloroform, the result was purified with column chromatography using ethyl acetate and hexane, and then distilled and dried to prepare Compound 1-1 (39.4 g, yield 51%; MS: [M+H]$^+$=347).

2) Synthesis of Compound 1-2

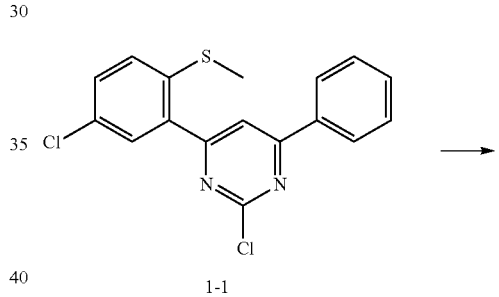

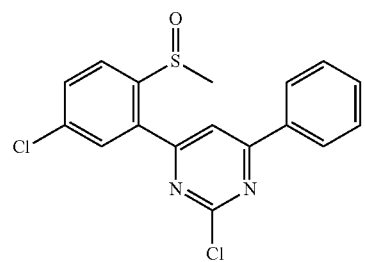

After introducing acetic acid (300 mL) to Compound 1-1 (39.4 g, 113.8 mmol), 35% hydrogen peroxide (11.4 g) was introduced thereto, and the result was stirred for 5 hours at room temperature. To the reaction material, an aqueous NaOH solution was introduced, and after stirring the result for 20 minutes, ethyl acetate was introduced thereto, and the water layer was removed. The result was dried with anhydrous magnesium sulfate, vacuum concentrated and then dried to prepare Compound 1-2 (41.2 g, yield 100%, MS: [M+H]$^+$=363).

3) Synthesis of Compound 1-3

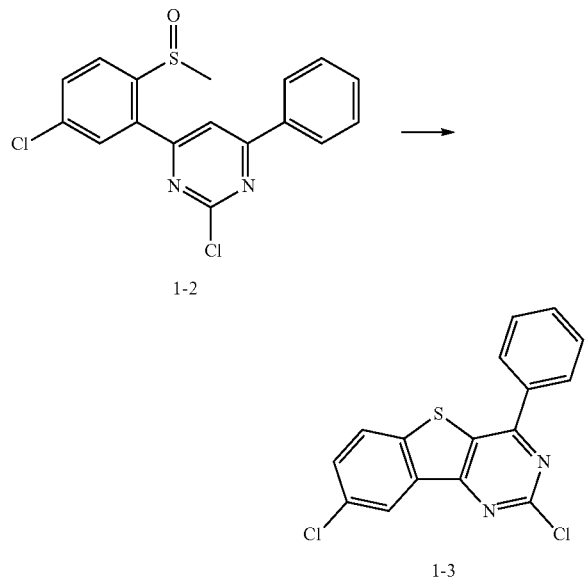

Compound 1-2 (36.4 g, 101 mmol) was introduced to sulfuric acid (150 mL), and the result was stirred for 24 hours at room temperature. To the reaction material, a cold aqueous NaOH solution was introduced, and after stirring the result for 30 minutes, chloroform was added thereto for layer separation, and the result was washed 3 times with water. The result was dried with anhydrous magnesium sulfate, vacuum concentrated, then recrystallized using a mixed solution of tetrahydrofuran and ethyl acetate, and then dried to prepare Compound 1-3 (30.4 g, yield 81%, MS: [M+H]$^+$=331).

4) Synthesis of Compound 1-4

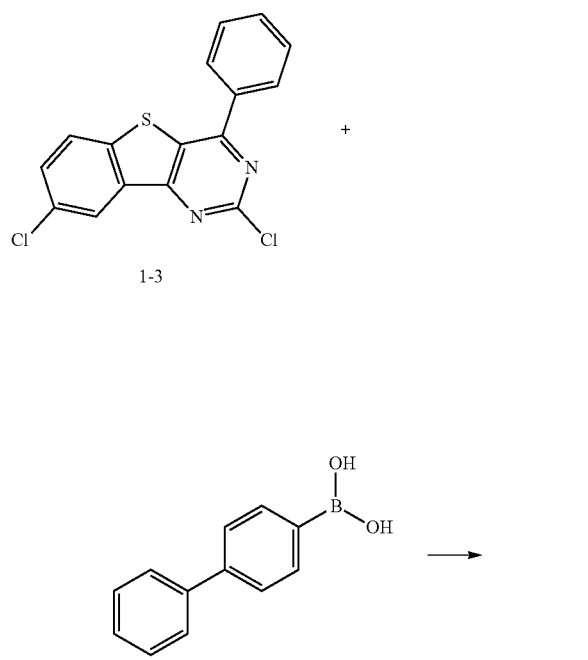

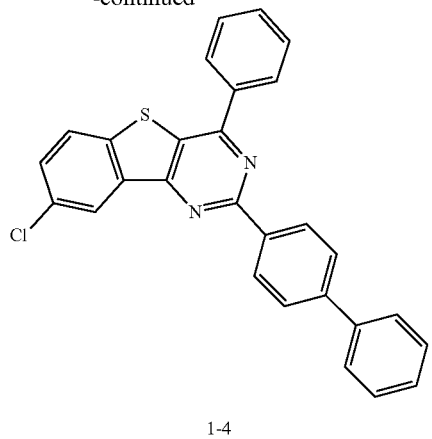

After dispersing Compound 1-3 (30.4 g, 92.1 mmol) and [1,1'-biphenyl]-4-ylboronic acid (20.1 g, 101.3 mmol) into tetrahydrofuran (250 ml), a 2 M aqueous potassium carbonate solution (aq. K$_2$CO$_3$) (138 ml) and then tetrakis(triphenyl-phosphine)palladium(0) [Pd(PPh$_3$)$_4$] (3.2 g, 3 mol %) were added thereto, and the result was stirred under reflux for 4 hours. The temperature was lowered to room temperature, and produced solids were filtered. The filtered solids were recrystallized with tetrahydrofuran and ethyl acetate, filtered, and then dried to prepare Compound 1-4 (28.9 g, yield 70%; MS: [M+H]$^+$=449).

4) Synthesis of Compound 1-5

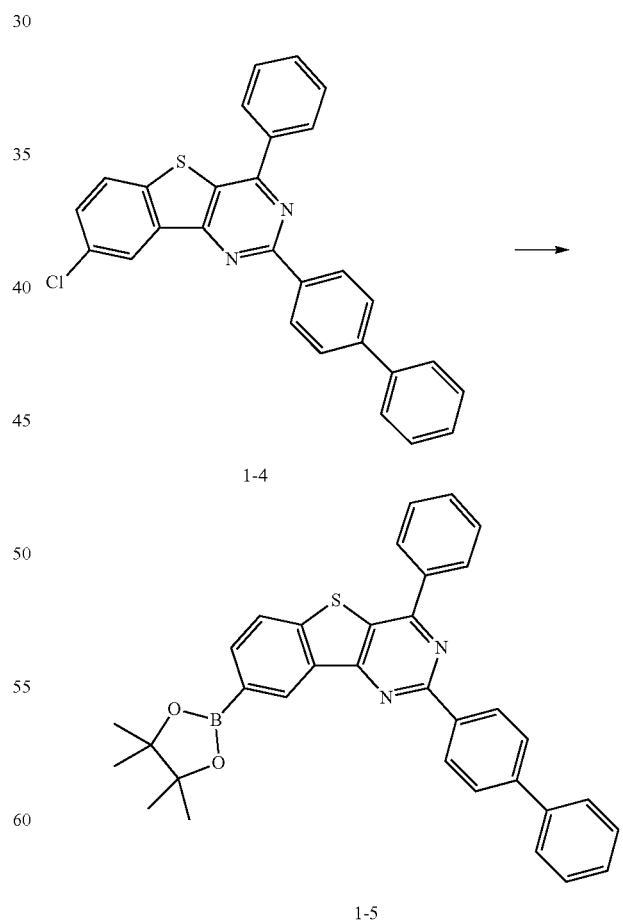

Compound 1-4 (28.9 g, 64.5 mmol), bis(pinacolato)diboron (18.0 g, 70.9 mmol), potassium acetate (19.0 g, 193.4 mmol), dibenzylideneacetone palladium (1.1 g, 1.9 mmol) and tricyclohexylphosphine (1.1 g, 3.8 mmol) were introduced to dioxane (300 ml), and refluxed for 12 hours. After the reaction was finished, the result was cooled to room temperature and then vacuum distilled to remove the solvent. This was dissolved in chloroform, washed 3 times with water, and the organic layer was separated and dried with magnesium sulfate. This was recrystallized using ethyl acetate while being vacuum distilled to prepare Compound 1-5 (22.6 g, yield 65%; MS: $[M+H]^+=541$).

5) Synthesis of Compound 1

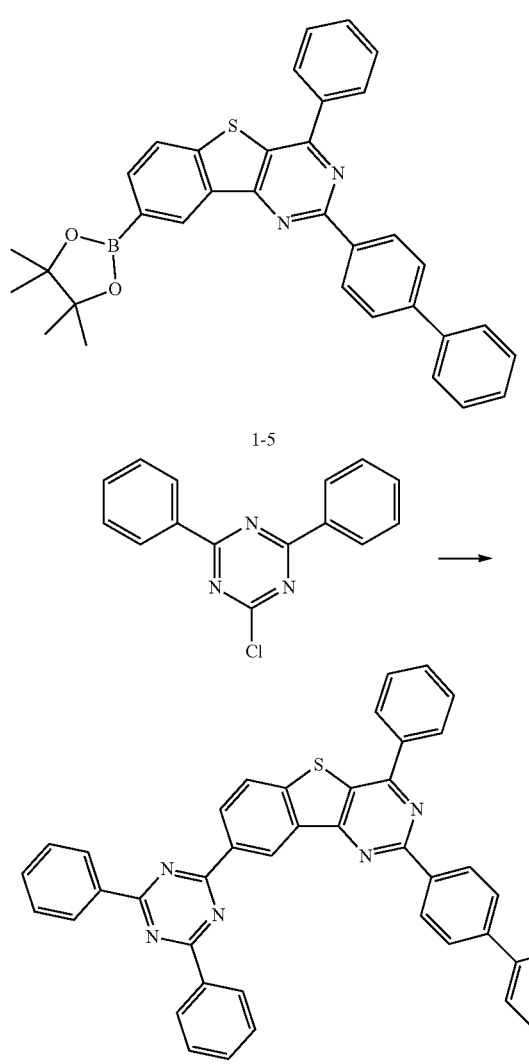

Compound 1

After dispersing Compound 1-5 (15.0 g, 27.1 mmol) and 2-chloro-4,6-diphenyl-1,3,5-triazine (7.2 g, 27.11 mmol) into tetrahydrofuran (150 ml), a 2 M aqueous potassium carbonate solution (aq. $K_2CO_3$) (40 ml) and then tetrakis (triphenyl-phosphine)palladium(0) $[Pd(PPh_3)_4]$ (0.9 g, 3 mol %) were added thereto, and the result was stirred under reflux for 4 hours. The temperature was lowered to room temperature, and produced solids were filtered. The filtered solids were recrystallized with tetrahydrofuran and ethyl acetate, filtered, and then dried to prepare Compound 1 (5.3 g, yield 30%; MS: $[M+H]^+=646$).

Preparation Example 2

1) Synthesis of Compound 2-1

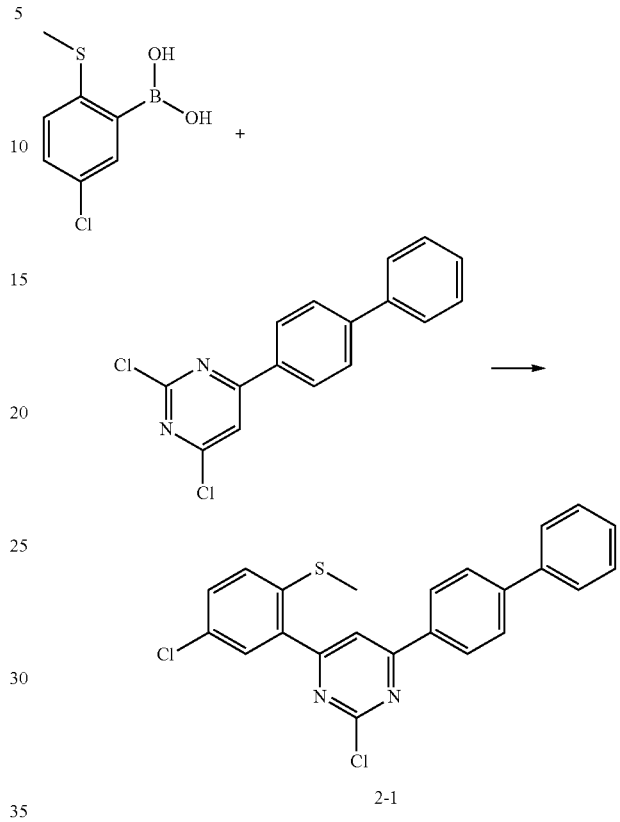

2-1

After dispersing 4-([1,1'-biphenyl]-4-yl)-2,6-dichloro-pyrimidine (50.0 g, 223.2 mmol) and (3-chloro-2-(methylthio)-phenyl)boronic acid (67.0 g, 223.2 mmol) into tetrahydrofuran (500 ml), a 2 M aqueous potassium carbonate solution (aq. $K_2CO_3$) (335 ml) and then tetrakis(triphenylphosphine)-palladium(0) $[Pd(PPh_3)_4]$ (7.7 g, 3 mol %) were added thereto, and the result was stirred under reflux for 5 hours. After lowering the temperature to room temperature, the result was separated into an organic layer and a water layer, and the organic layer was distilled. The distilled organic material was extracted with chloroform and water, and after distilling the chloroform, the result was purified with column chromatography using ethyl acetate and hexane, and then distilled and dried to prepare Compound 2-1 (44.3 g, yield 47%; MS: $[M+H]^+=423$).

2) Synthesis of Compound 2-2

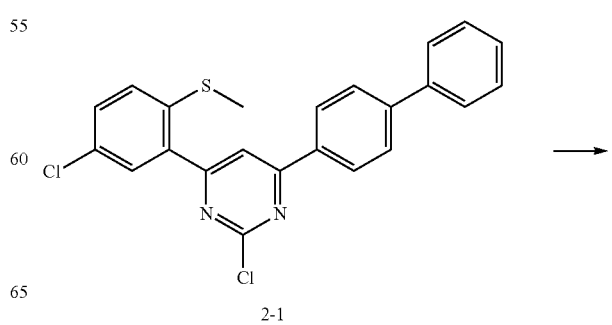

2-1

-continued

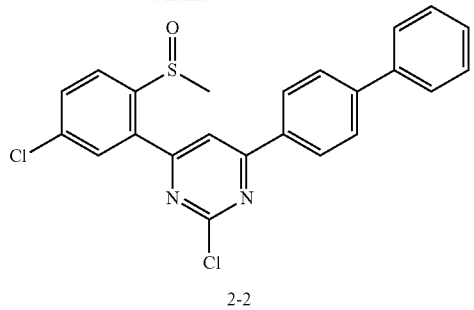

2-2

After introducing acetic acid (500 mL) to Compound 2-1 (44.3 g, 105.0 mmol), 35% hydrogen peroxide (11.9 g) was introduced thereto, and the result was stirred for 5 hours at room temperature. To the reaction material, an aqueous NaOH solution was introduced, and after stirring the result for 20 minutes, ethyl acetate was introduced thereto, and the water layer was removed. The result was dried with anhydrous magnesium sulfate, vacuum concentrated and then dried to prepare Compound 2-2 (46.0 g, yield 100%, MS: $[M+H]^+=439$).

3) Synthesis of Compound 2-3

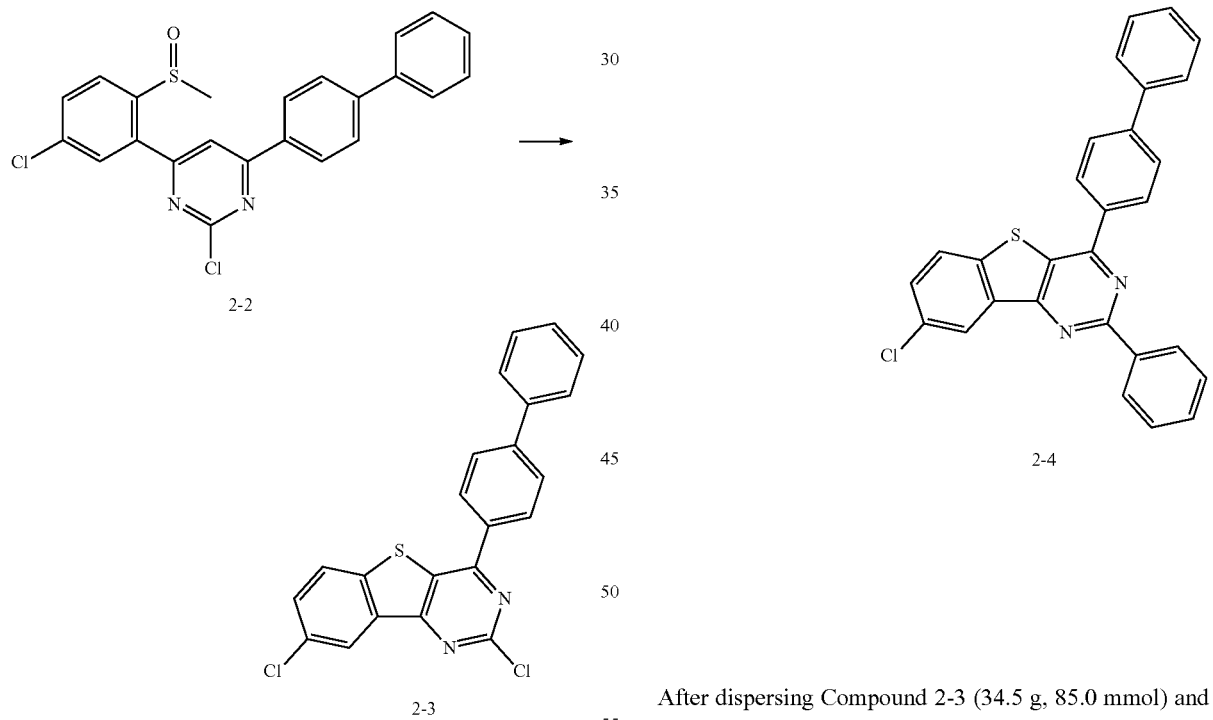

Compound 2-2 (52.7 g, 105.0 mmol) was introduced to sulfuric acid (200 mL), and the result was stirred for 24 hours at room temperature. To the reaction material, a cold aqueous NaOH solution was introduced, and after stirring the result for 30 minutes, chloroform was added thereto for layer separation, and the result was washed 3 times with water. The result was dried with anhydrous magnesium sulfate, vacuum concentrated, then recrystallized using a mixed solution of tetrahydrofuran and ethyl acetate, and then dried to prepare Compound 2-3 (34.5 g, yield 81%, MS: $[M+H]^+=407$).

4) Synthesis of Compound 2-4

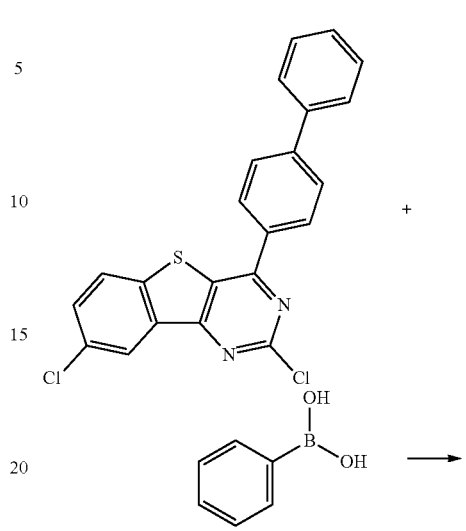

After dispersing Compound 2-3 (34.5 g, 85.0 mmol) and phenylboronic acid (11.4 g, 93.5 mmol) into tetrahydrofuran (300 ml), a 2 M aqueous potassium carbonate solution (aq. $K_2CO_3$) (128 ml) and then tetrakis(triphenylphosphine)-palladium(0) [Pd(PPh$_3$)$_4$] (2.9 g, 3 mol %) were added thereto, and the result was stirred under reflux for 4 hours. The temperature was lowered to room temperature, and produced solids were filtered. The filtered solids were recrystallized with tetrahydrofuran and ethyl acetate, filtered, and then dried to prepare Compound 2-4 (33.5 g, yield 88%; MS: $[M+H]^+=449$).

5) Synthesis of Compound 2-5

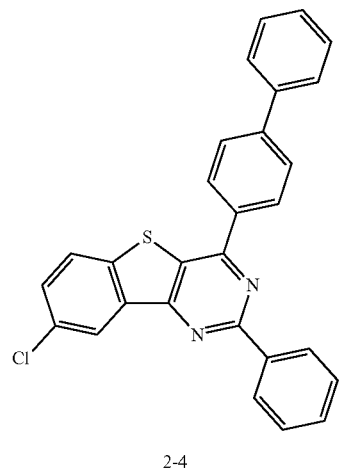

2-4

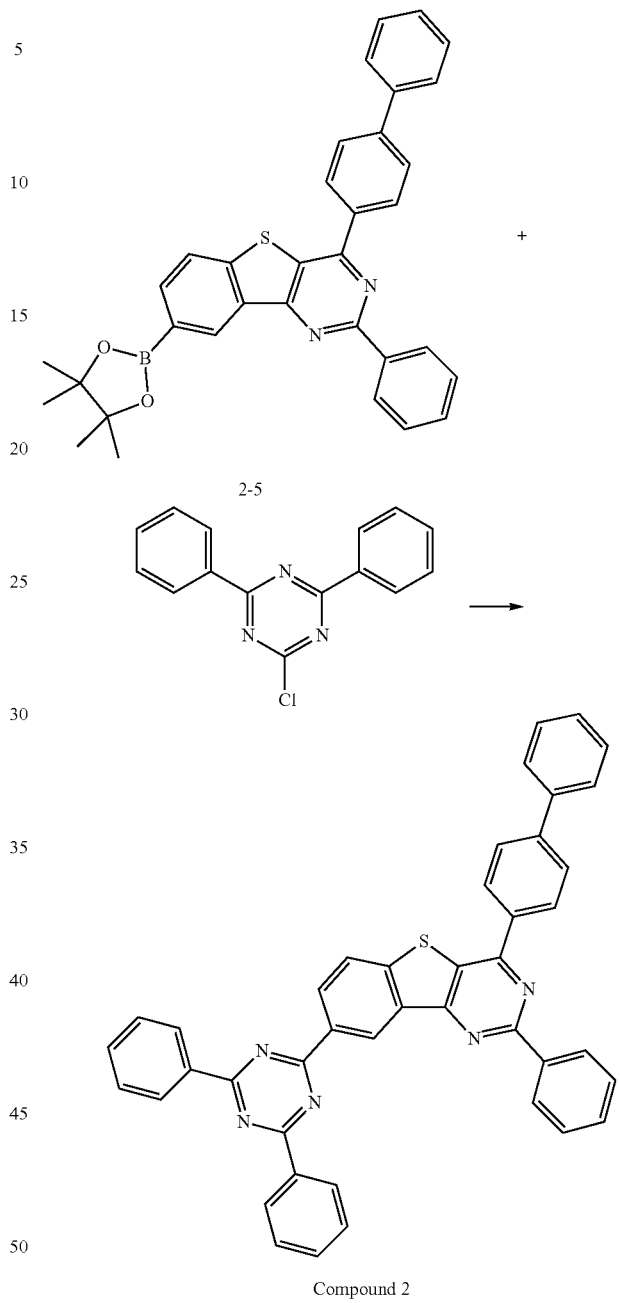

6) Synthesis of Compound 2

Compound 2-4 (33.5 g, 74.8 mmol), bis(pinacolato)diboron (20.9 g, 82.4 mmol), potassium acetate (22.0 g, 224.3 mmol), dibenzylideneacetone palladium (1.3 g, 2.2 mmol) and tricyclohexylphosphine (1.3 g, 4.5 mmol) were introduced to dioxane (200 ml), and refluxed for 12 hours. After the reaction was finished, the result was cooled to room temperature and then vacuum distilled to remove the solvent. This was dissolved in chloroform, washed 3 times with water, and the organic layer was separated and dried with magnesium sulfate. This was recrystallized using ethyl acetate while being vacuum distilled to prepare Compound 2-5 (31.9 g, yield 79%; MS: [M+H]$^+$=541).

After dispersing Compound 2-5 (15.0 g, 27.1 mmol) and 2-chloro-4,6-diphenyl-1,3,5-triazine (7.2 g, 27.1 mmol) into tetrahydrofuran (150 ml), a 2 M aqueous potassium carbonate solution (aq. $K_2CO_3$) (40 ml) and then tetrakis(triphenylphosphine)palladium(0) [Pd(PPh$_3$)$_4$] (0.9 g, 3 mol %) were added thereto, and the result was stirred under reflux for 4 hours. The temperature was lowered to room temperature, and produced solids were filtered. The filtered solids were recrystallized with tetrahydrofuran and ethyl acetate, filtered, and then dried to prepare Compound 2 (14.1 g, yield 79%; MS: [M+H]$^+$=646).

Preparation Example 3

1) Synthesis of Compound 3-1

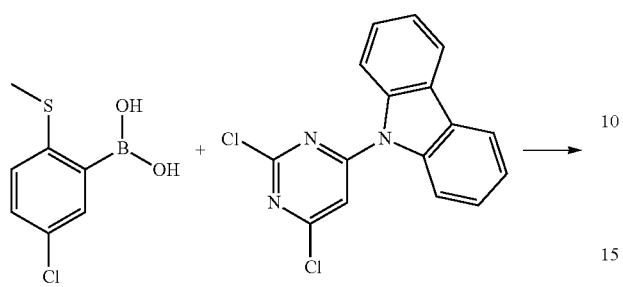

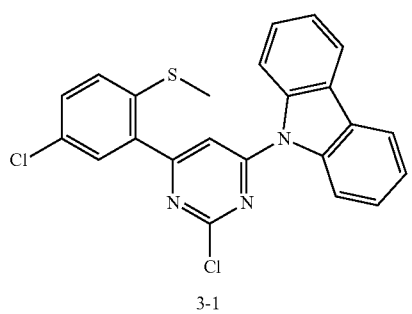

3-1

After dispersing 9-(2,6-dichloropyrimidin-4-yl)-9H-carbazole (50.0 g, 223.2 mmol) and (3-chloro-2-(methylthio)phenyl)boronic acid (69.9 g, 223.2 mmol) into tetrahydrofuran (500 ml), a 2 M aqueous potassium carbonate solution (aq. K$_2$CO$_3$) (335 ml) and then tetrakis(triphenyl-phosphine)palladium(0) [Pd(PPh$_3$)$_4$] (7.7 g, 3 mol %) were added thereto, and the result was stirred under reflux for 5 hours. After lowering the temperature to room temperature, the result was separated into an organic layer and a water layer, and the organic layer was distilled. The distilled organic material was extracted with chloroform and water, and after distilling the chloroform, the result was purified with column chromatography using ethyl acetate and hexane, and then distilled and dried to prepare Compound 3-1 (46.5 g, yield 47%; MS: [M+H]$^+$=436).

2) Synthesis of Compound 3-2

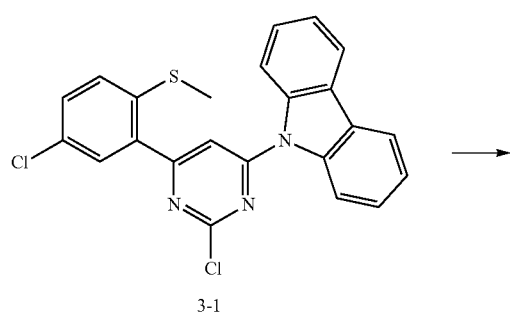

3-1

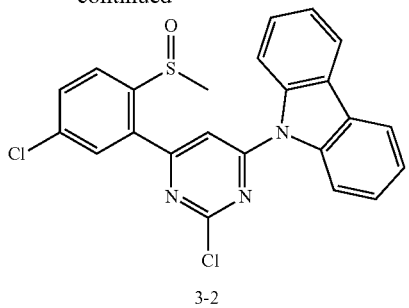

3-2

After introducing acetic acid (400 mL) to Compound 3-1 (46.5 g, 106.9 mmol), 35% hydrogen peroxide (12.1 g) was introduced thereto, and the result was stirred for 5 hours at room temperature. To the reaction material, an aqueous NaOH solution was introduced, and after stirring the result for 20 minutes, ethyl acetate was introduced thereto, and the water layer was removed. The result was dried with anhydrous magnesium sulfate, vacuum concentrated and then dried to prepare Compound 3-2 (48.3 g, yield 100%, MS: [M+H]$^+$=452).

3) Synthesis of Compound 3-3

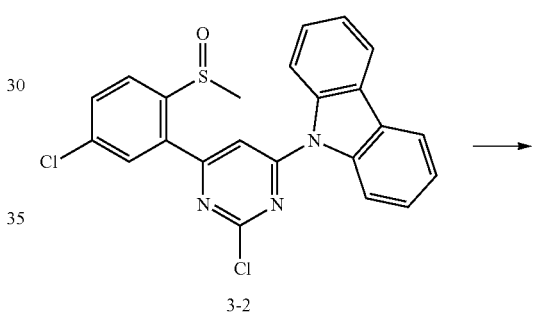

3-2

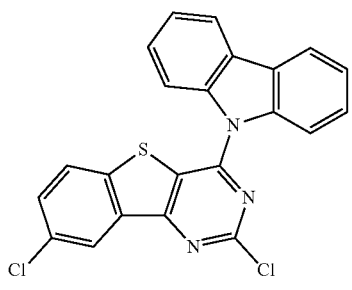

3-3

Compound 3-2 (48.3 g, 107.1 mmol) was introduced to sulfuric acid (200 mL), and the result was stirred for 24 hours at room temperature. To the reaction material, a cold aqueous NaOH solution was introduced, and after stirring the result for 30 minutes, chloroform was added thereto for layer separation, and the result was washed 3 times with water. The result was dried with anhydrous magnesium sulfate, vacuum concentrated, then recrystallized using a mixed solution of tetrahydrofuran and ethyl acetate, and then dried to prepare Compound 3-3 (29.3 g, yield 66%, MS: [M+H]$^+$=420).

4) Synthesis of Compound 3-4

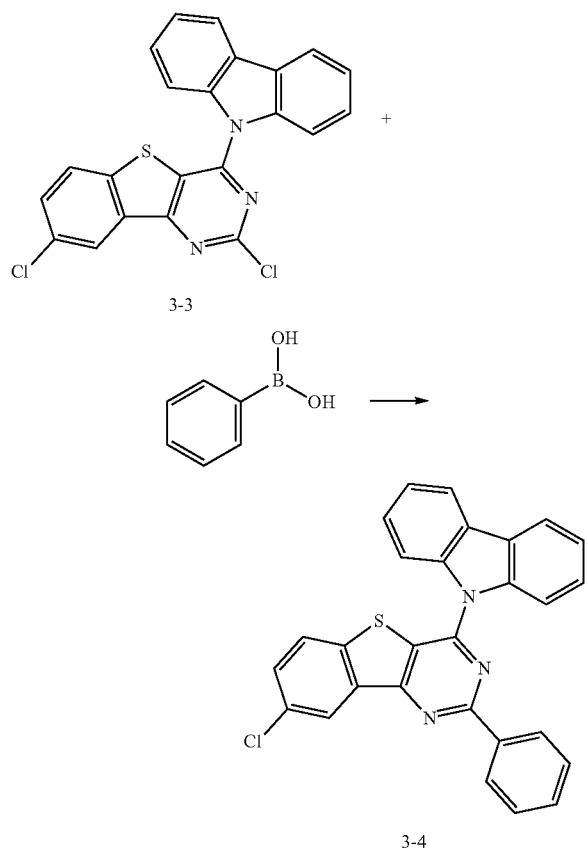

After dispersing Compound 3-3 (29.3 g, 67.0 mmol) and phenylboronic acid (9.6 g, 76.8 mmol) into tetrahydrofuran (300 ml), a 2 M aqueous potassium carbonate solution (aq. K₂CO₃) (105 ml) and then tetrakis(triphenylphosphine)-palladium(0) [Pd(PPh₃)₄] (2.4 g, 3 mol %) were added thereto, and the result was stirred under reflux for 4 hours. The temperature was lowered to room temperature, and produced solids were filtered. The filtered solids were recrystallized with tetrahydrofuran and ethyl acetate, filtered, and then dried to prepare Compound 3-4 (24.8 g, yield 78%; MS: [M+H]⁺=462).

5) Synthesis of Compound 3-5

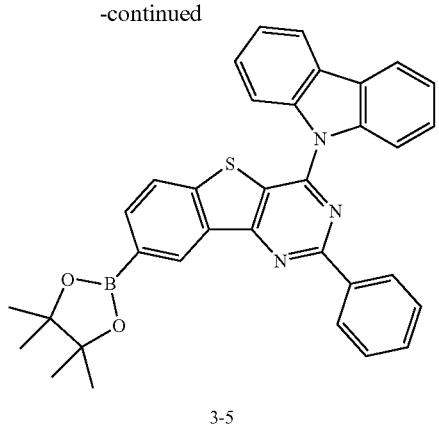

Compound 3-4 (24.8 g, 53.8 mmol) bis(pinacolato)diboron (15.1 g, 59.1 mmol), potassium acetate (15.8 g, 160.7 mmol), dibenzylideneacetone palladium (0.9 g, 1.6 mmol) and tricyclohexylphosphine (0.9 g, 3.2 mmol) were introduced to dioxane (300 ml), and refluxed for 12 hours. After the reaction was finished, the result was cooled to room temperature and then vacuum distilled to remove the solvent. This was dissolved in chloroform, washed 3 times with water, and the organic layer was separated and dried with magnesium sulfate. This was recrystallized using ethyl acetate while being vacuum distilled to prepare Compound 3-5 (16.2 g, yield 55%; MS: [M+H]⁺=554).

6) Synthesis of Compound 3

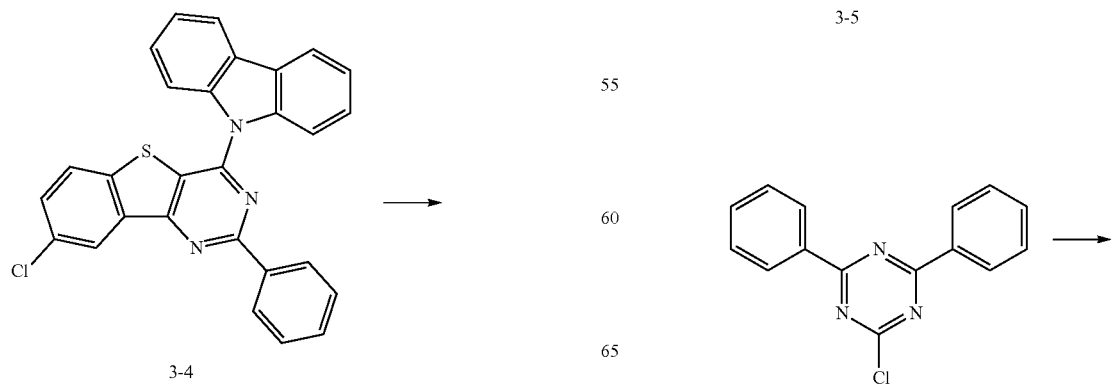

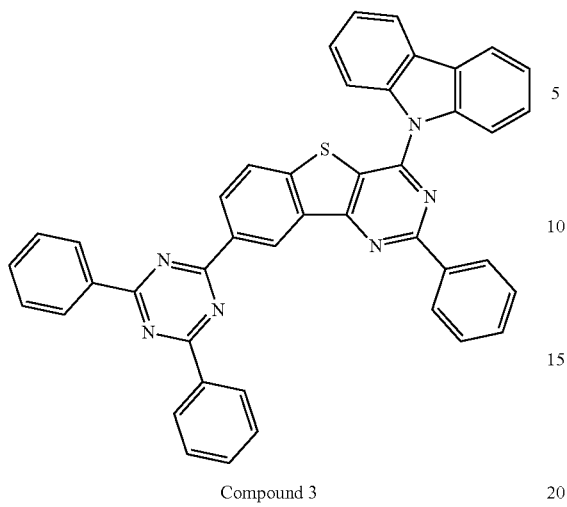

Compound 3

After dispersing Compound 3-5 (15.0 g, 27.1 mmol) and 2-chloro-4,6-diphenyl-1,3,5-triazine (7.2 g, 27.1 mmol) into tetrahydrofuran (150 ml), a 2 M aqueous potassium carbonate solution (aq. K$_2$CO$_3$) (40 ml) and then tetrakis(triphenylphosphine)palladium(0) [Pd(PPh$_3$)$_4$] (1.6 g, 3 mol %) were added thereto, and the result was stirred under reflux for 4 hours. The temperature was lowered to room temperature, and produced solids were filtered. The filtered solids were recrystallized with tetrahydrofuran and ethyl acetate, filtered, and then dried to prepare Compound 3 (12.7 g, yield 71%; MS: [M+H]$^+$=659).

Preparation Example 4

1) Synthesis of Compound 4-1

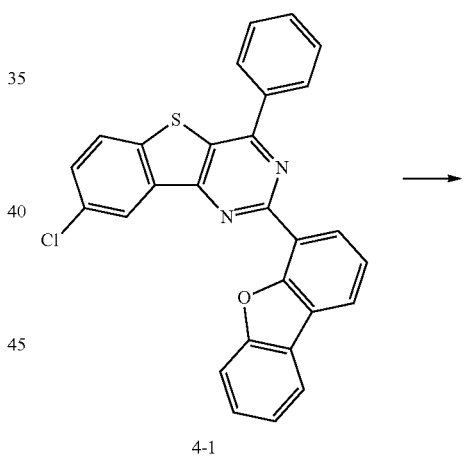

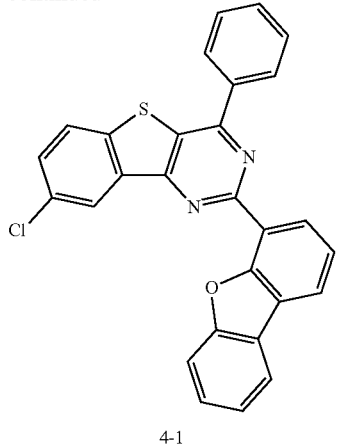

4-1

After dispersing Compound 1-3 (20.0 g, 60.8 mmol) and dibenzo[b,d]furan-4-ylboronic acid (14.2 g, 66.9 mmol) into tetrahydrofuran (200 ml), a 2 M aqueous potassium carbonate solution (aq. K$_2$CO$_3$) (91 ml) and then tetrakis(triphenylphosphine)palladium(0) [Pd(PPh$_3$)$_4$] (2.1 g, 3 mol %) were added thereto, and the result was stirred under reflux for 4 hours. The temperature was lowered to room temperature, and produced solids were filtered. The filtered solids were recrystallized with tetrahydrofuran and ethyl acetate, filtered, and then dried to prepare Compound 4-1 (15.4 g, yield 55%; MS: [M+H]$^+$=463)

2) Synthesis of Compound 4-2

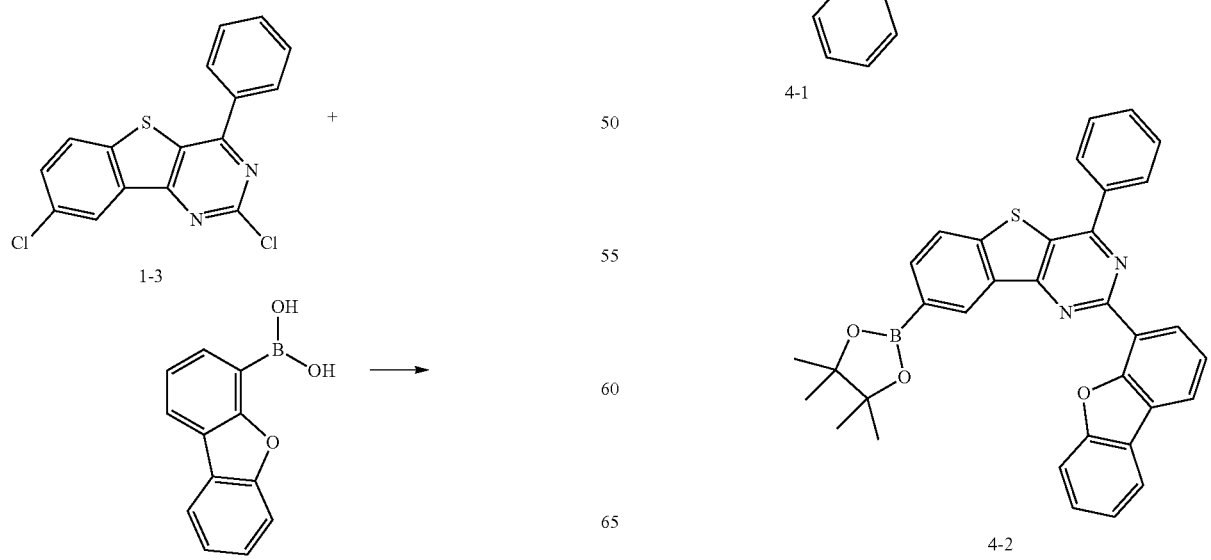

4-1

4-2

Compound 4-1 (15.4 g, 33.3 mmol) bis(pinacolato)diboron (9.3 g, 36.7 mmol), potassium acetate (9.8 g, 100.0 mmol), dibenzylideneacetone palladium (0.6 g, 1.0 mmol) and tricyclohexylphosphine (0.6 g, 1.0 mmol) were introduced to dioxane (200 ml), and refluxed for 12 hours. After the reaction was finished, the result was cooled to room temperature and then vacuum distilled to remove the solvent. This was dissolved in chloroform, washed 3 times with water, and the organic layer was separated and dried with magnesium sulfate. This was recrystallized using ethyl acetate while being vacuum distilled to prepare Compound 4-2 (16.4 g, yield 89%; MS: [M+H]$^+$=555).

3) Synthesis of Compound 4

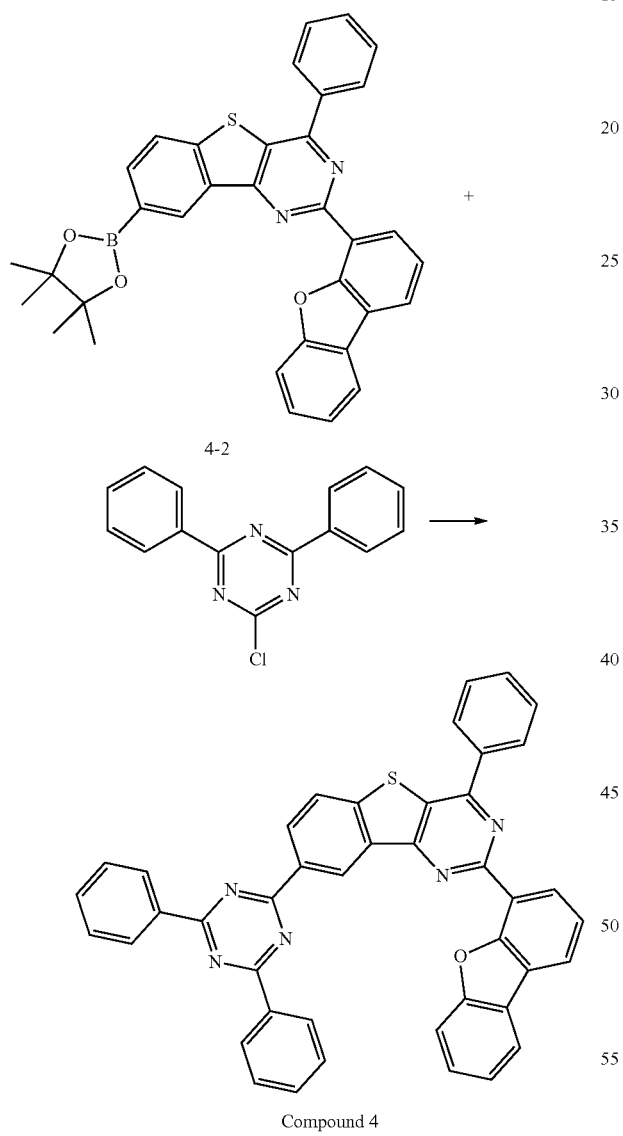

After dispersing Compound 4-2 (15.0 g, 27.1 mmol) and 2-chloro-4,6-diphenyl-1,3,5-triazine (7.2 g, 27.1 mmol) into tetrahydrofuran (150 ml), a 2 M aqueous potassium carbonate solution (aq. K$_2$CO$_3$) (40 ml) and then tetrakis(triphenylphosphine)palladium(0) [Pd(PPh$_3$)$_4$] (0.9 g, 3 mol %) were added thereto, and the result was stirred under reflux for 4 hours. The temperature was lowered to room temperature, and produced solids were filtered. The filtered solids were recrystallized with tetrahydrofuran and ethyl acetate, filtered, and then dried to prepare Compound 4 (7.8 g, yield 44%; MS: [M+H]$^+$=670).

Preparation Example 5

1) Synthesis of Compound 5-1

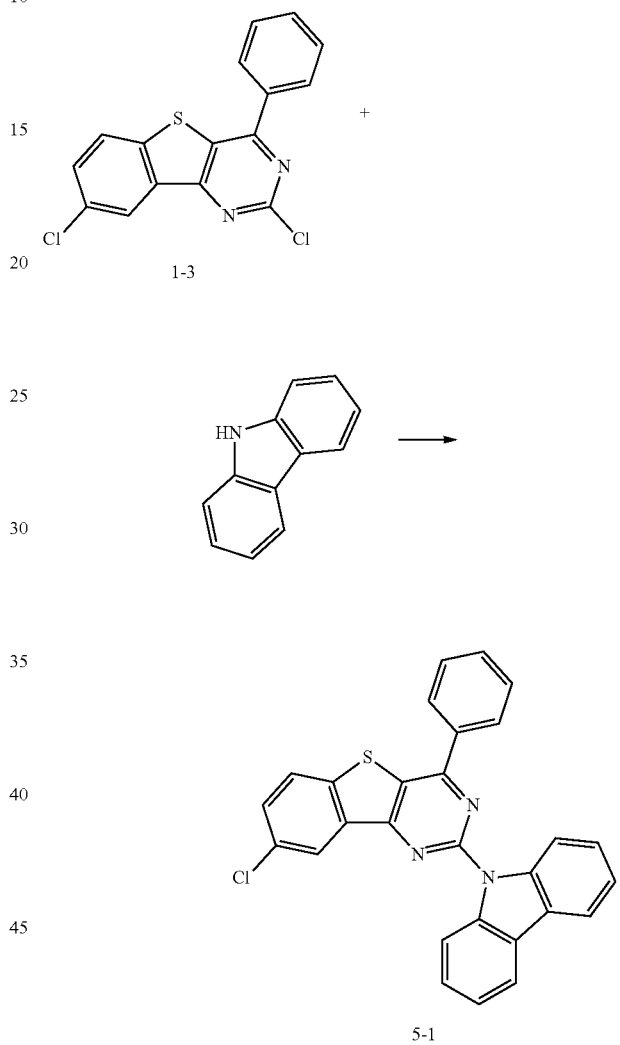

Compound 1-3 (20.0 g, 60.8 mmol) and 9H-carbazole (10.2 g, 60.8 mmol) were introduced to xylene (200 mL) for dissolution, and sodium tertiary-butoxide (17.5 g, 182.4 mmol) was added thereto, and the temperature was raised. Bis(tri-tertiarybutylphosphine)palladium (1.0 g, 3 mol %) was introduced thereto, and the result was stirred under reflux for 12 hours. When the reaction was completed, the temperature was lowered to room temperature, and produced solids were filtered. The solids were dissolved in chloroform (700 mL), and after washed twice with water, the organic layer was separated, stirred after introducing anhydrous magnesium sulfate thereto, and filtered, and the filtrate was vacuum distilled. The concentrated compound was purified through silica column using chloroform and ethyl acetate to prepare Compound 5-1 (16.5 g, 59%; MS: [M+H]$^+$=463) in a light green solid form.

2) Synthesis of Compound 5-2

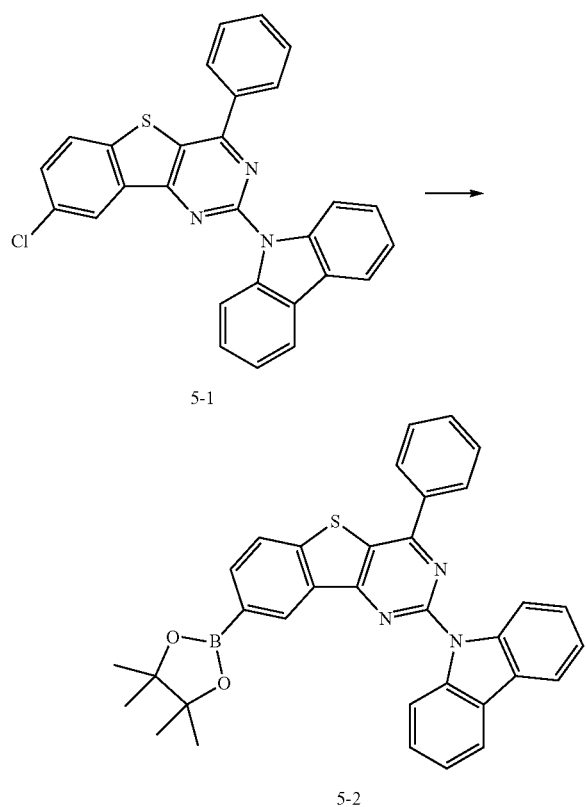

5-1

5-2

Compound 5-1 (16.5 g, 35.9 mmol) bis(pinacolato)diboron (10.0 g, 39.5 mmol), potassium acetate (10.6 g, 107.6 mmol), dibenzylideneacetone palladium (0.6 g, 1.1 mmol) and tricyclohexylphosphine (0.6 g, 2.1 mmol) were introduced to dioxane (200 ml), and refluxed for 12 hours. After the reaction was finished, the result was cooled to room temperature and then vacuum distilled to remove the solvent. This was dissolved in chloroform, washed 3 times with water, and the organic layer was separated and dried with magnesium sulfate. This was recrystallized using ethyl acetate while being vacuum distilled to prepare Compound 5-2 (16.5 g, yield 83%; MS: [M+H]$^+$=555).

3) Synthesis of Compound 5

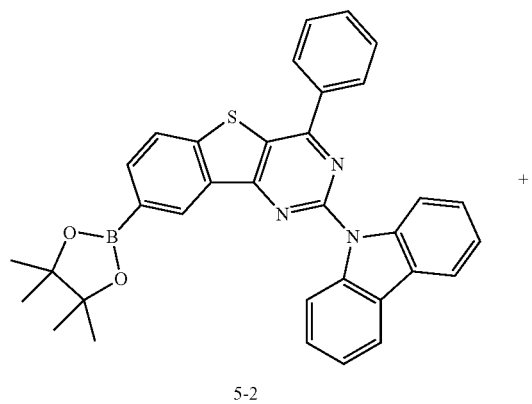

5-2

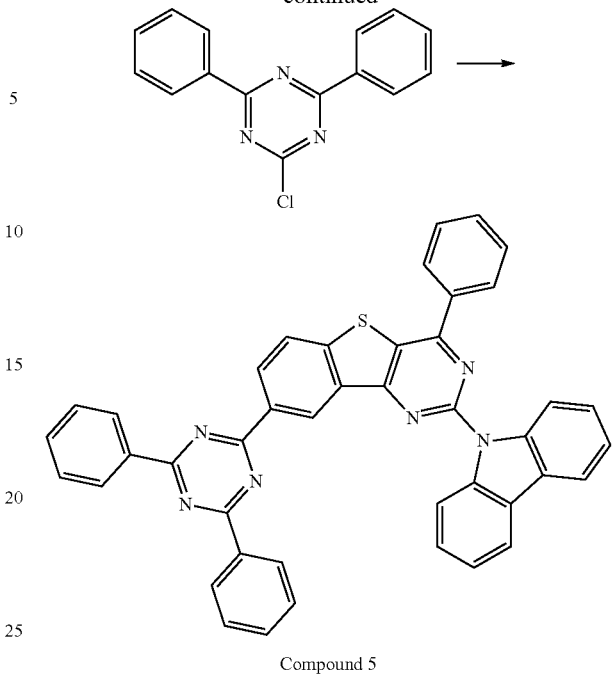

Compound 5

After dispersing Compound 5-2 (15.0 g, 27.1 mmol) and 2-chloro-4,6-diphenyl-1,3,5-triazine (7.2 g, 27.1 mmol) into tetrahydrofuran (150 ml), a 2 M aqueous potassium carbonate solution (aq. K$_2$CO$_3$) (40 ml) and then tetrakis(triphenyl-)phosphine)palladium(0) [Pd(PPh$_3$)$_4$] (0.9 g, 3 mol %) were added thereto, and the result was stirred under reflux for 4 hours. The temperature was lowered to room temperature, and produced solids were filtered. The filtered solids were recrystallized with tetrahydrofuran and ethyl acetate, filtered, and then dried to prepare Compound 5 (5.9 g, yield 33%; MS: [M+H]$^+$=670).

Experimental Examples

Experimental Example 1

A glass substrate on which indium tin oxide (ITO) was coated as a thin film to a thickness of 1,300 Å was placed in distilled water containing dissolved detergent and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. The substrate was cleaned for 5 minutes using oxygen plasma, and then transferred to a vacuum deposition apparatus.

On the transparent ITO electrode prepared as above, a hole injection layer was formed by thermal vacuum depositing the following HI-1 compound to a thickness of 50 Å. On the hole injection layer, a hole transfer layer was formed by thermal vacuum depositing the following HT-1 compound to a thickness of 250 Å, and on the HT-1 deposited film, an electron blocking layer was formed by vacuum depositing the following HT-2 compound to a thickness of 50 Å. On the HT-2 deposited film, Compound 1 prepared in advance in Preparation Example 1, the following YGH-1 compound and phosphorescent dopant YGD-1 were co-deposited in a weight ratio of 44:44:12 to form a light emitting layer having a thickness of 400 Å. An electron transfer layer was formed on the light emitting layer by vacuum depositing the following ET-1 compound to a thickness of 250 Å, and on the electron transfer layer, an electron injection layer having a thickness of 100 Å was formed by vacuum depositing the following ET-2 compound and Li in a weight ratio of 98:2. A cathode was formed on the electron injection layer by depositing aluminum to a thickness of 1000 Å.

HI-1

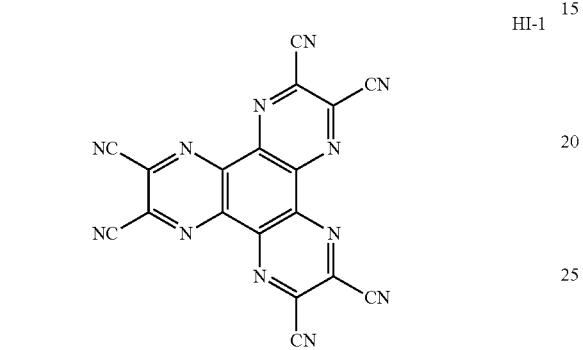

HT-1

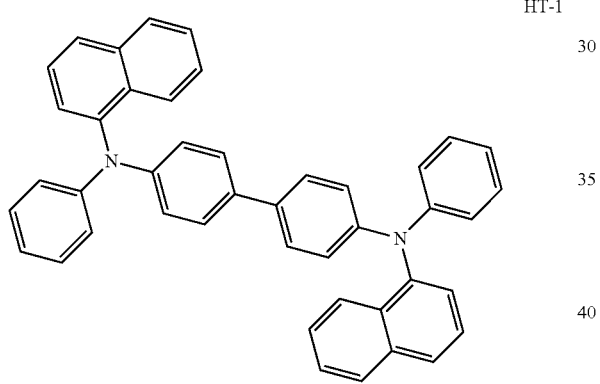

HT-2

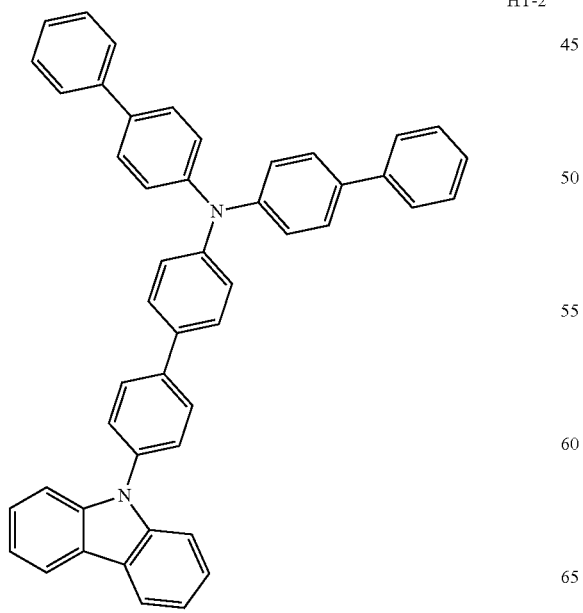

YGH-1

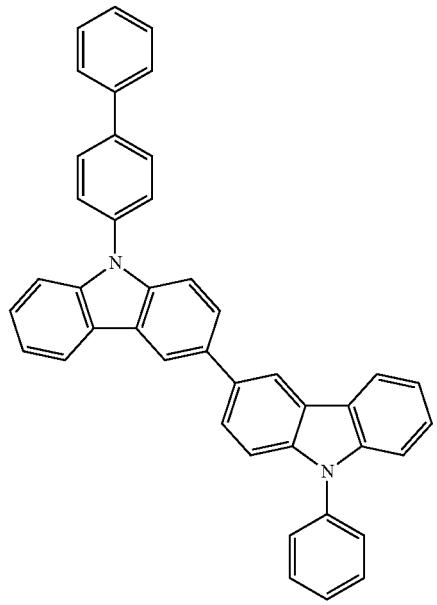

YGD-1

ET-1

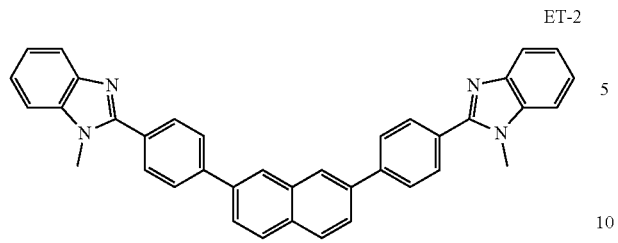

ET-2

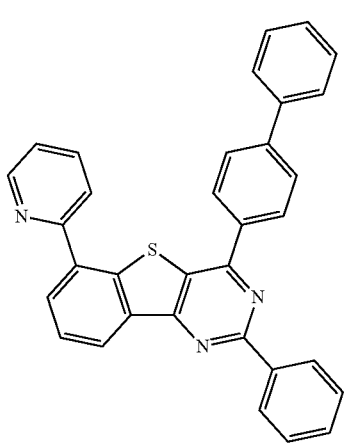

CE2

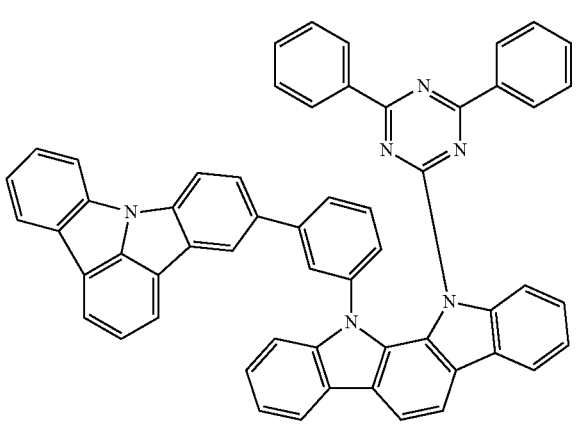

CE3

In the above-mentioned process, the deposition rates of the organic materials were maintained at 0.4 Å/sec to 0.7 Å/sec, the deposition rate of the aluminum was maintained at 2 Å/sec, and the degree of vacuum during the deposition was maintained at $1\times10^{-7}$ torr to $5\times10^{-8}$ torr.

Experimental Examples 2 to 5

Organic light emitting devices were manufactured in the same manner as in Experimental Example 1 except that compounds described in the following Table 1 were used instead of Compound 1 of Preparation Example 1.

Comparative Experimental Examples 1 to 4

Organic light emitting devices were manufactured in the same manner as in Experimental Example 1 except that compounds described in the following Table 1 were used instead of Compound 1 of Preparation Example 1. Compounds of CE1 to CE4 of the following Table 1 are as follows:

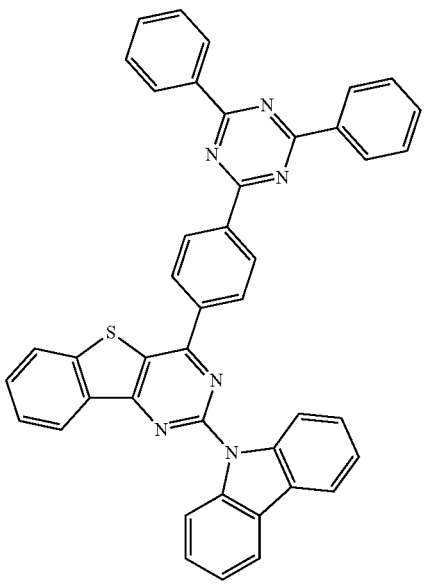

CE4

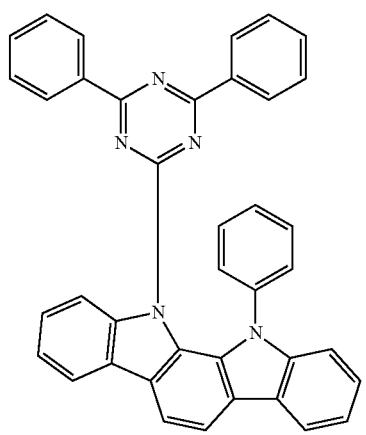

CE1

For the organic light emitting devices manufactured in the experimental examples and the comparative experimental examples, voltage and efficiency were measured at current density of 10 mA/cm², and a lifetime was measured at current density of 50 mA/cm². The results are shown in the following Table 1. As used herein, $LT_{95}$ means the time taken for luminance becoming 95% with respect to initial luminance.

TABLE 1

| Compound | Voltage (V) (@10 mA/cm$^2$) | Efficiency (Cd/A) (@10 mA/cm$^2$) | Color Coordinate (x, y) | Lifetime (h) ($LT_{95}$) at 50 mA/cm$^2$ |
| --- | --- | --- | --- | --- |
| Experimental Example 1 | Compound 1 | 4.3 | 83 | 0.45, 0.54 | 90 |
| Experimental Example 2 | Compound 2 | 3.9 | 81 | 0.46, 0.53 | 120 |
| Experimental Example 3 | Compound 3 | 4.2 | 80 | 0.45, 0.53 | 150 |
| Experimental Example 4 | Compound 4 | 3.8 | 83 | 0.45, 0.54 | 125 |
| Experimental Example 5 | Compound 5 | 3.9 | 83 | 0.45, 0.54 | 160 |
| Comparative Experimental Example 1 | CE1 | 4.5 | 70 | 0.46, 0.54 | 80 |
| Comparative Experimental Example 2 | CE2 | 6.0 | 34 | 0.48, 0.50 | 10 |
| Comparative Experimental Example 3 | CE3 | 5.5 | 74 | 0.45, 0.57 | 30 |
| Comparative Experimental Example 4 | CE4 | 4.9 | 80 | 0.44, 0.55 | 15 |

As shown in Table 1, it was identified that, when using the compound of the present disclosure as a light emitting layer material, properties of excellent efficiency and lifetime were obtained compared to the comparative experimental examples. This is due to excellent material stability obtained by bonding benzothiopyrimidine to a triazine unit, which leads to excellent device efficiency, lifetime or the like. In addition, it was seen that those additionally substituted with a carbazole group had excellent lifetime properties, and those substituted with only an aryl substituent had excellent efficiency.

The invention claimed is:

1. A compound of Chemical Formula 1:

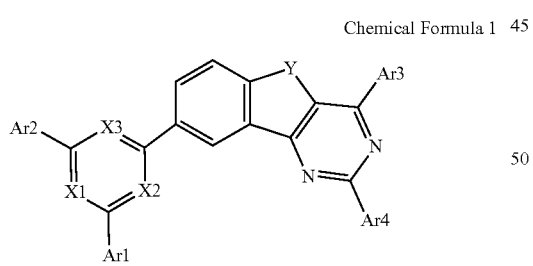

Chemical Formula 1 wherein, in Chemical Formula 1:
Y is O or S;
X1 to X3 are each N or CH, and one or more of X1 to X3 are N; and
Ar1 to Ar4 are the same as or different from each other, and each independently is an aryl group having 6 to 20 carbon atoms that is unsubstituted or substituted with nitrile or a heteroaryl group having 2 to 20 carbon atoms; or a tricyclic heteroaryl group having 2 to 20 carbon atoms that is unsubstituted or substituted with an aryl group having 6 to 20 carbon atoms.

2. The compound of claim 1, wherein X1 to X3 are N.

3. The compound of claim 1, wherein X1 is CH, and X2 and X3 are N; or X2 is CH, and X1 and X3 are N.

4. The compound of claim 1, wherein Ar1 to Ar4 are the same as or different from each other, and each independently is:
a phenyl group that is unsubstituted or substituted with a nitrile group or a carbazole group, or
a biphenyl group, or
a carbazole group, or
a dibenzofuran group, or
a dibenzothiophene group.

5. The compound of claim 1, wherein the compound of Chemical Formula 1 is selected from among the following compounds:

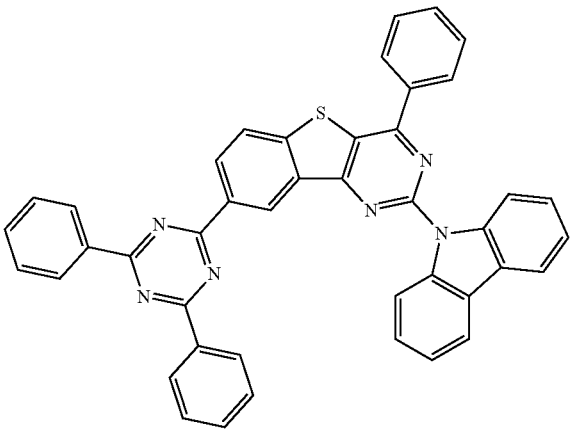

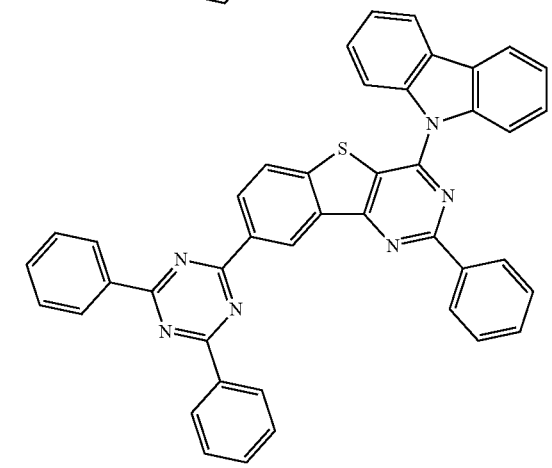

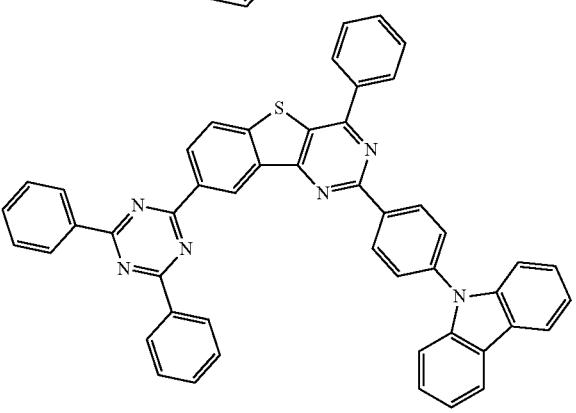

43
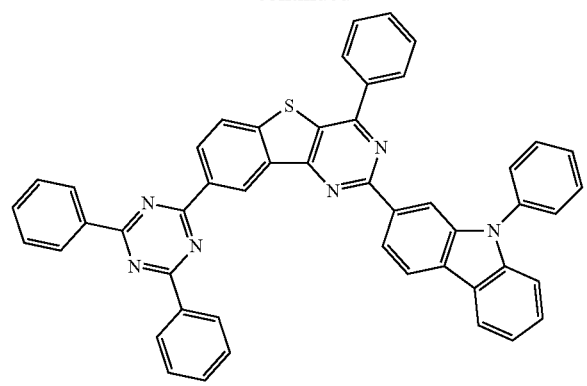
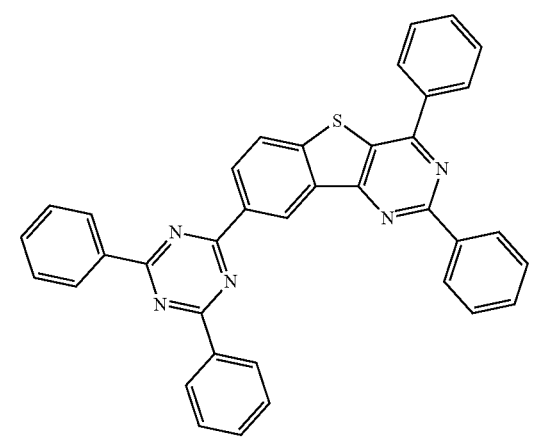
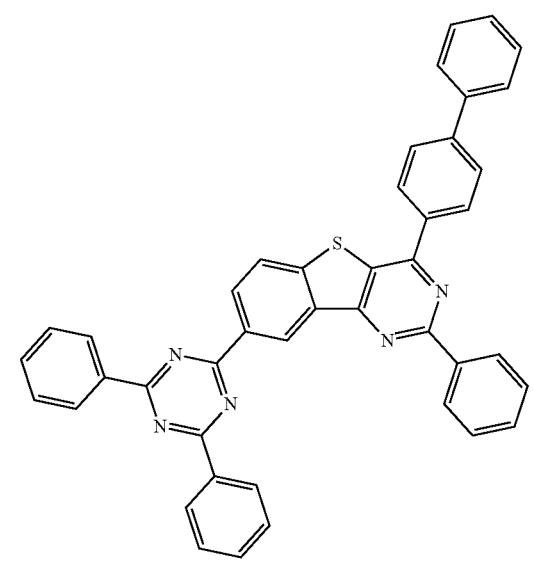
44
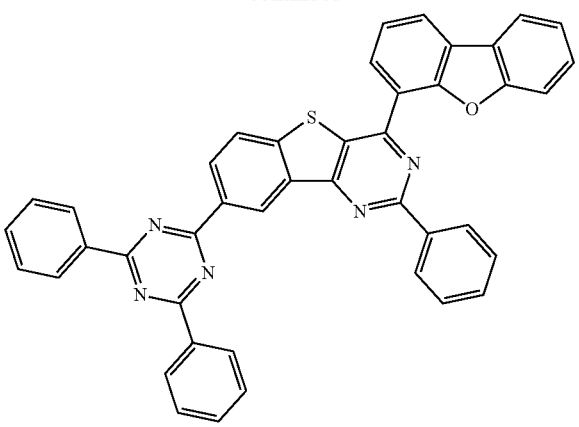
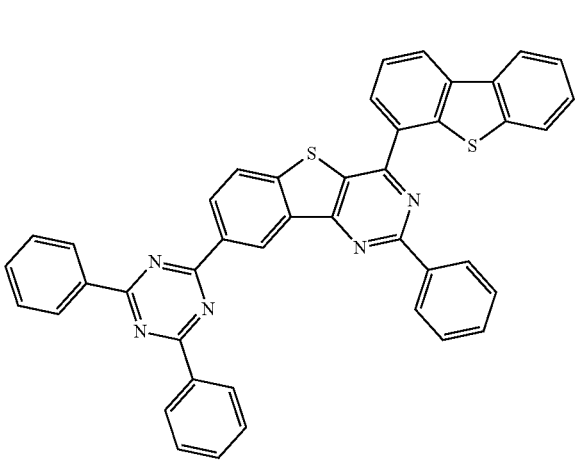
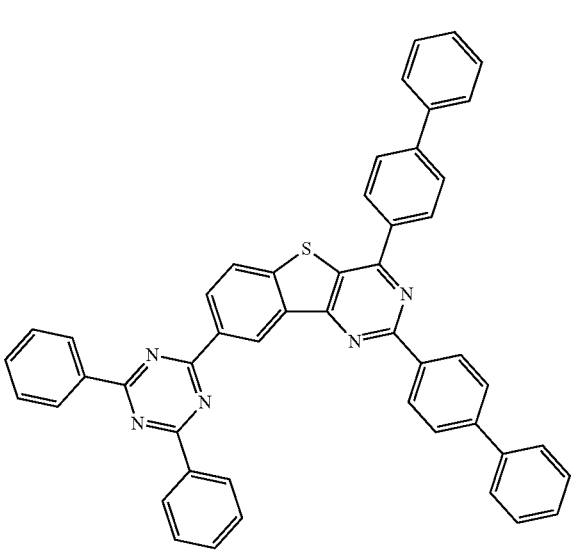

45
-continued
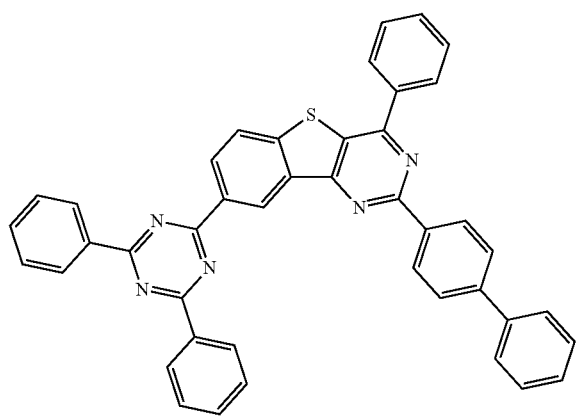
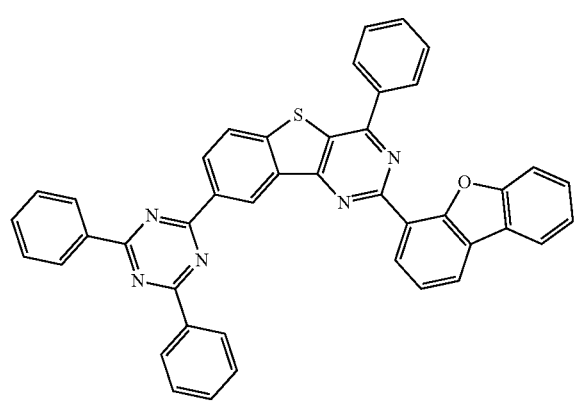
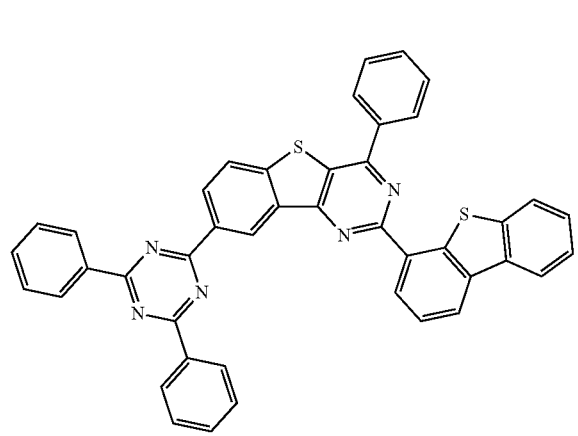
46
-continued
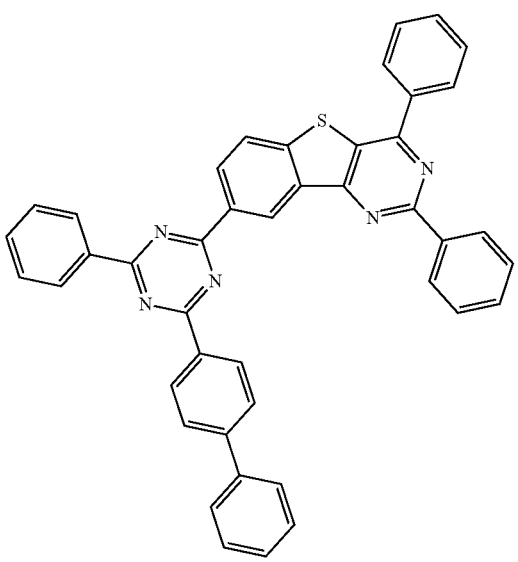
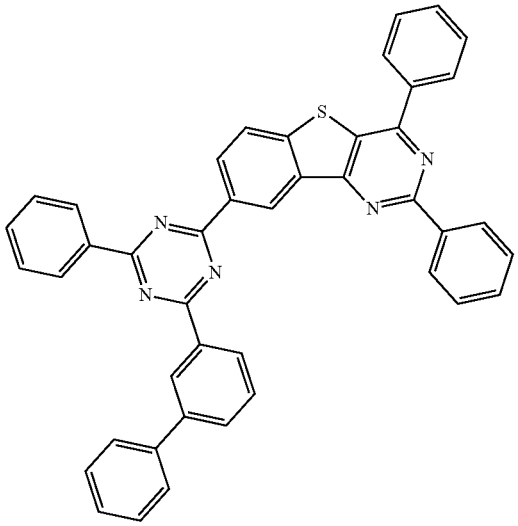
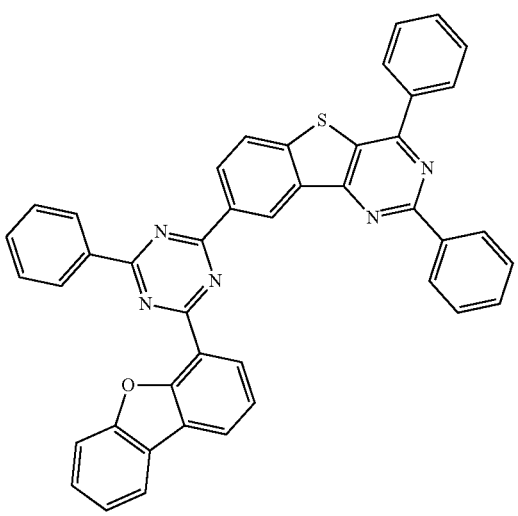

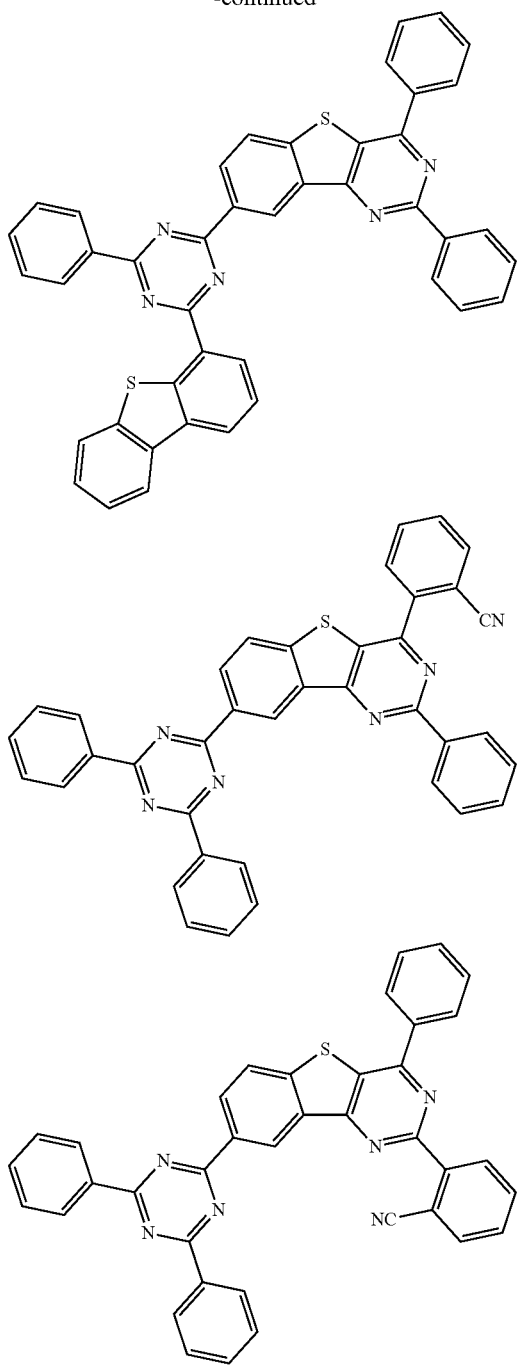

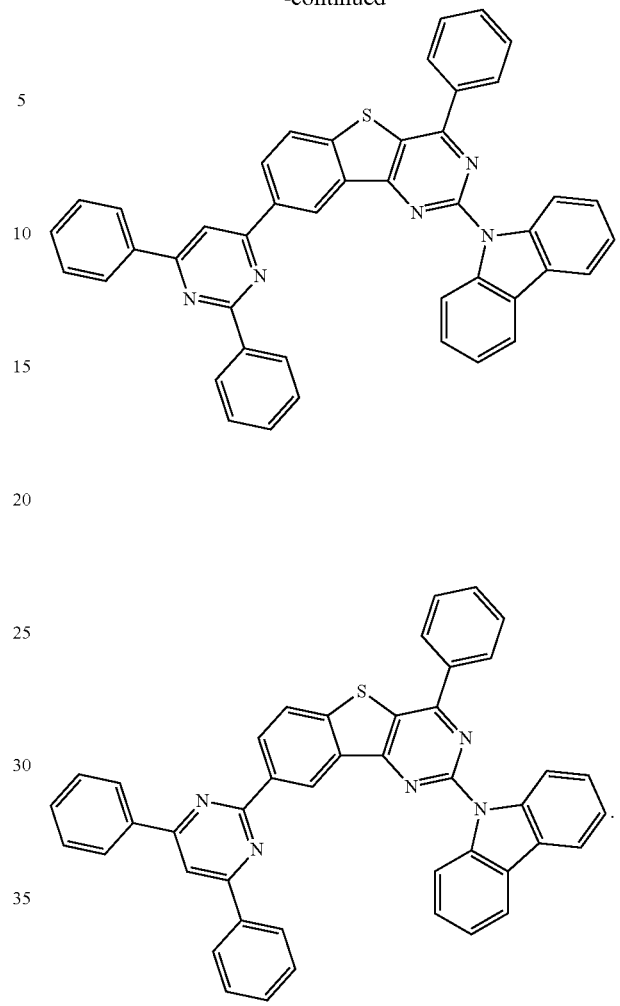

6. An organic light emitting device comprising:
   a first electrode;
   a second electrode provided opposite to the first electrode; and
   one, two or more organic material layers provided between the first electrode and the second electrode,
   wherein one or more layers of the organic material layers include the compound of claim 1.

7. The organic light emitting device of claim 6, wherein the organic material layer including the compound includes a light emitting layer, and the light emitting layer includes the compound.

* * * * *